United States Patent
Gatto et al.

(10) Patent No.: US 11,335,078 B2
(45) Date of Patent: May 17, 2022

(54) SYSTEM, METHOD AND COMPUTER PROGRAM

(71) Applicant: Sony Corporation, Tokyo (JP)

(72) Inventors: Alexander Gatto, Stuttgart (DE); Piergiorgio Sartor, Stuttgart (DE); Ralf Müller, Stuttgart (DE); Mori Hironori, Stuttgart (DE); Oliver Erdler, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 339 days.

(21) Appl. No.: 16/485,455

(22) PCT Filed: Feb. 28, 2018

(86) PCT No.: PCT/EP2018/054931
§ 371 (c)(1),
(2) Date: Aug. 13, 2019

(87) PCT Pub. No.: WO2018/162297
PCT Pub. Date: Sep. 13, 2018

(65) Prior Publication Data
US 2020/0042817 A1 Feb. 6, 2020

(30) Foreign Application Priority Data
Mar. 7, 2017 (EP) .................................. 17159717.2

(51) Int. Cl.
*G06V 10/143* (2022.01)
*G01N 21/31* (2006.01)
(Continued)

(52) U.S. Cl.
CPC .......... *G06V 10/143* (2022.01); *G01N 21/31* (2013.01); *G01N 33/14* (2013.01); *G06V 20/68* (2022.01)

(58) Field of Classification Search
USPC .................. 382/110, 141; 356/239.6; 702/25
See application file for complete search history.

(56) References Cited

U.S. PATENT DOCUMENTS 5,542,004 A * 7/1996 Constant .............. G01N 33/146
 382/100
6,275,603 B1 * 8/2001 Cronshaw .......... G01N 21/9027
 250/223 B
(Continued)

FOREIGN PATENT DOCUMENTS

WO 2016/081831 A1 5/2016
WO 2016/196504 A1 12/2016

OTHER PUBLICATIONS

Shiba Kata, Yoshikawa Genki: "Aero-Thermo-Dynamic Mass Analysis",Nature Nature, Jul. 1, 2016 (Jul. 1, 2016),DOI: 10.1038/srep28849 Retrieved from the Internet:URL:https://www.nature.com/articles/srep28849.pdf [retrieved on Jul. 29, 2021].
(Continued)

*Primary Examiner* — Kathleen Y Dulaney
(74) *Attorney, Agent, or Firm* — Xsensus LLP

(57) ABSTRACT

A system including circuitry configured to determine a reflectance feature of a liquid based on reflectance image data generated based on multispectral image data of the liquid; determine a structural feature of the liquid based on image data of the liquid; and to provide quality information of the liquid based on the reflectance feature and the structural feature.

21 Claims, 18 Drawing Sheets

(51) Int. Cl.
 *G01N 33/14* (2006.01)
 *G06V 20/68* (2022.01)

(56) References Cited

U.S. PATENT DOCUMENTS

| | | | |
|---|---|---|---|
| 6,374,845 B1 | 4/2002 | Melendez et al. | |
| 6,439,035 B1* | 8/2002 | Yasui | G01N 33/146 |
| | | | 250/223 B |
| 6,753,527 B1* | 6/2004 | Yamagishi | G01F 23/2921 |
| | | | 250/339.06 |
| 6,819,811 B1 | 11/2004 | Goldstein | |
| 7,355,694 B2* | 4/2008 | Yasui | G01N 13/00 |
| | | | 356/239.4 |
| 7,704,457 B2 | 4/2010 | Patton | |
| 7,840,360 B1* | 11/2010 | Micheels | G01N 21/359 |
| | | | 702/25 |
| 8,228,489 B2 | 7/2012 | Suzuki et al. | |
| 8,305,570 B2* | 11/2012 | Piana | G01N 21/51 |
| | | | 356/239.6 |
| 2002/0154809 A1* | 10/2002 | Yamagishi | G01N 21/909 |
| | | | 382/142 |
| 2003/0214649 A1* | 11/2003 | Yagita | G01N 21/9027 |
| | | | 356/239.5 |
| 2004/0126279 A1 | 7/2004 | Renzi et al. | |
| 2006/0210139 A1* | 9/2006 | Carroll | G01N 13/02 |
| | | | 382/141 |
| 2009/0162042 A1 | 6/2009 | Wexler et al. | |
| 2010/0302540 A1* | 12/2010 | Piana | G01N 21/51 |
| | | | 356/337 |
| 2012/0281096 A1* | 11/2012 | Gellaboina | G01F 23/2962 |
| | | | 348/163 |
| 2014/0367483 A1 | 12/2014 | Jackson et al. | |
| 2016/0069743 A1* | 3/2016 | McQuilkin | G01N 21/31 |
| | | | 356/416 |
| 2017/0053393 A1 | 2/2017 | Tzao et al. | |
| 2017/0089236 A1* | 3/2017 | Andersen | F01M 11/04 |
| 2017/0262729 A1* | 9/2017 | Penna | A47J 43/12 |
| 2018/0321066 A1* | 11/2018 | Cooper | G01F 1/007 |
| 2019/0200799 A1* | 7/2019 | Mes | G06F 3/1259 |
| 2019/0307287 A1* | 10/2019 | Magatti | A47J 31/44 |

OTHER PUBLICATIONS

International Search Report and Written Opinion dated May 24, 2018 for PCT/EP2018/054931 filed on Feb. 28, 2018, 8 pages.

Ocean Optics, "Spark Spectral Sensor for Reagent Measurements", 2016, pp. 1-8.

Engelhard et al., "OPQS—Optical Process and Quality Sensing. Exemplary applications in the beer brewing and polyurethane foaming processes", University of Potsdam, Institute of Chemistry & Interdisciplinary Center of Photonics, 2006, pp. 1-17.

Andor, "Absorption / Transmission / Reflection Spectroscopy", An introduction to Absorption / Transmission /Reflection Spectroscopy, 2 pages.

* cited by examiner

SYSTEM, METHOD AND COMPUTER PROGRAM

CROSS-REFERENCE TO RELATED APPLICATIONS

The present application is based on PCT filing PCT/EP2018/054931, filed Feb. 28, 2018, which claims priority to EP 17159717.2, filed Mar. 7, 2017, the entire contents of each are incorporated herein by reference.

TECHNICAL FIELD

The present disclosure relates to the field of computer vision, in particular to systems, methods and computer programs for identification of liquids, e.g. beverages.

TECHNICAL BACKGROUND

In computer vision, mathematical techniques are used to detect the presence of and recognize various items that are depicted in digital images. Computer vision tasks include methods for acquiring, processing, analyzing and understanding digital images, and in general deal with the extraction of high-dimensional data from the real world in order to produce numerical or symbolic information, e.g., in the forms of decisions. Localized portions of an image, on which specific types of computations are performed to produce visual features, may be used to analyze and classify objects depicted in the image. Low-level features, such as interest points and edges, edge distributions, color distributions, shapes and shape distributions, may be computed from portions of an image and used to detect items that are depicted in the image. Machine learning algorithms can be used for feature recognition.

Accurate identification of liquids/beverages being consumed is an important task to for example people who suffer from food-born allergies, who participate in weight-loss programs, and who just enjoy drinking and trying new beverages.

In order to judge the quality of liquids/beverages, invasive approaches are required which normally involve the cooperation of laboratories and thus are on one side very time consuming and on the other side very expensive.

SUMMARY

According to a first aspect, the disclosure provides a system including circuitry configured to determine a reflectance feature of a liquid based on a reflectance image generated based on multispectral image data of the liquid; determine a structural feature of the liquid based on image data of the liquid; and to provide quality information of the liquid based on the reflectance feature and the structural feature.

According to a further aspect, the disclosure provides a method including determining a reflectance feature of a liquid based on a reflectance image generated based on multispectral image data of the liquid; determining a structural feature of the liquid based on image data of the liquid; and providing quality information of the liquid based on the reflectance feature and the structural feature.

According to a further aspect, the disclosure provides a computer program including instructions, the instructions when executed on a processor causing the processor to determine a reflectance feature of a liquid based on reflectance image generated based on multispectral image data of the liquid; determine a structural feature of the liquid based on image data of the liquid; and to provide quality information of the liquid based on the reflectance feature and the structural feature. Further aspects are set forth in the dependent claims, the following description and the drawings.

BRIEF DESCRIPTION OF THE DRAWINGS

Embodiments are explained by way of example with respect to the accompanying drawings, in which:

FIG. 9b illustrates a second measurement for obtaining a reflectance spectrum, wherein the light source of the mobile reflectometer is switched on;

DETAILED DESCRIPTION OF EMBODIMENTS

Figure 1:
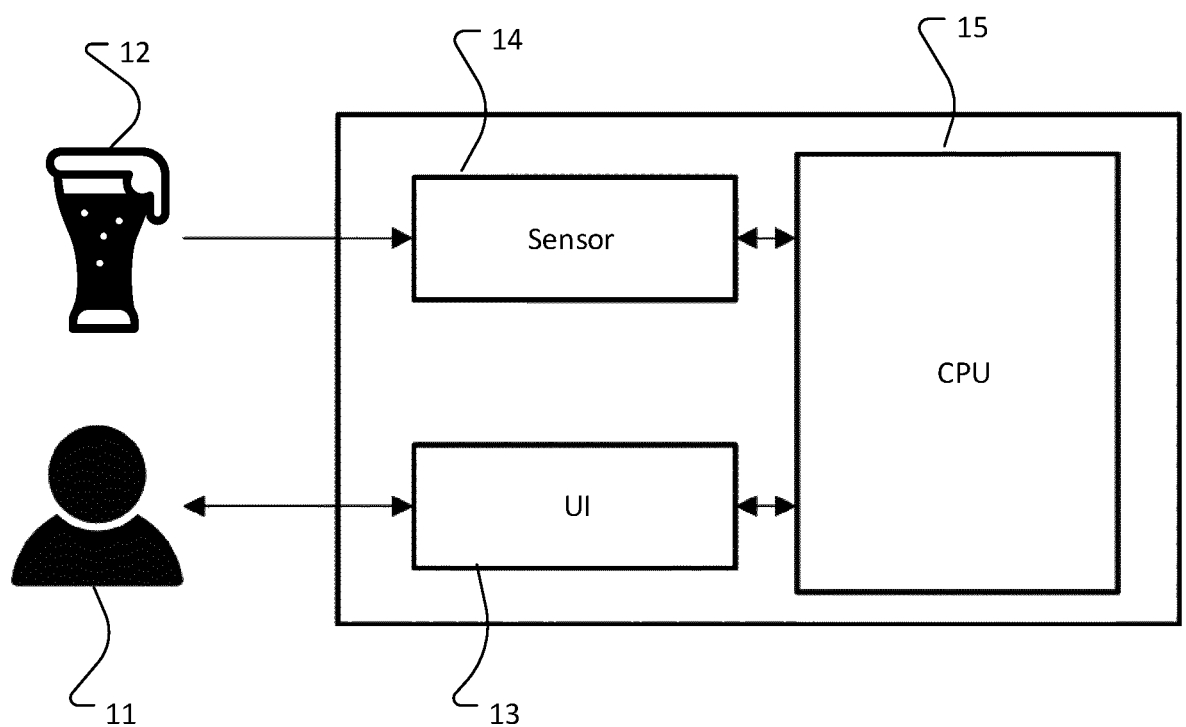
FIG. 1 schematically describes a system for beverage analysis.

Before a detailed description of the embodiments under reference of FIG. 1, general explanations are made.

Every day, billions of open drinks are served worldwide in restaurants, fast food restaurants, canteens or side walk sales. In general, the end-consumer can rely on the quality and safety of sold beverages but from time to time there are uncertainties. For example an end-consumer may call into question if the served beer is really fresh and the specific one which was ordered. He may call into question if the wine is as old as written on the menu and from the famous region which justifies the high price, or he may ask if a drink is free of allergens or other contaminations, if a cocktail contains as much alcohol as it should have or if it is it really free of alcohol. By means of the embodiments disclosed below, the end-consumer may get an answer to such questions in time to unworriedly enjoy his or her drink.

The embodiments described below provide a system including circuitry configured to determine a reflectance feature of a liquid based on reflectance image data generated based on multispectral image data of the liquid; determine a structural feature of the liquid based on RGB image data of the liquid; and to provide quality information of the liquid based on the reflectance feature and the structural feature.

Liquids may for example be any kind of liquids such as beverages or drinks intended for human consumption such as plain water, milk, juices, coffee, tea, beer and soft drinks. The term liquid shall also include medical infusions or the like. Still further, the term liquids shall also include liquids that in part include non-liquid components such as cocktails with a piece of lemon or the like.

The system may for example include mobile devices, smartphones, tablets, smartwatches, glasses or other kinds of wearable devices, liquid processing devices such as kitchen appliances, e.g. coffee machines, beer dispenser or the like. The system may also include any such devices in cooperation with a server or cloud processing and/or storage system. Still further, the system may also include a client device and a remote device, e.g. a server device, that are connected via a network such as the Internet or a LAN.

The circuitry may for example be implemented by a processor, e.g. a central processing unit (CPU) or the like. The processor may be located on a mobile device, a remote workstation or a cloud server. The circuitry may also be distributed circuitry that is distributed over a mobile device, a remote workstation, and/or a cloud server.

The multispectral image data may include first multispectral image data of a liquid without calibrated light and second multispectral image data of the liquid with calibrated light.

Accordingly, the circuitry may be configured to obtain the first multispectral image data of the liquid without calibrated light and the circuitry may be configured to obtain the second multispectral image data of the liquid with calibrated light.

A calibrated light spectrum may include information about the intensity in dependence on wavelength of light. The calibrated light spectrum may cover a predefined wavelength range, e.g. wavelength range of visible light, ultraviolet, and/or infrared light spectrum, etc. The calibrated light spectrum may have a predefined accuracy. The present disclosure is not limited to a specific form, accuracy, data form, or the like of the calibrated light spectrum.

A multispectral image may be obtained by a multispectral imaging device such as a multispectral camera. Spectral imaging may be a combination of imaging and spectroscopy, where a spectrum is collected at every location of an image plane. Multispectral imaging may include retrieving for each pixel multiple measurements, each measurement relating to a specific frequency in the frequency spectrum. Multispectral imaging is not restricted to visible light, but works also in ultraviolet and in infrared. A multispectral camera may for example capture measurements in the visible color channel from 400-700 nm and a near infrared (NIR) channel from 750-900+nm. Multispectral imaging may also include hyperspectral imaging.

The system may include circuitry that is configured to determine an analysis result based on the reflectance features. Such reflectance features may for example be obtained from reflectance image data (e.g. a reflectance image). A reflectance image may for example be calculated based on a spectral image that is obtained by image subtraction of a first multispectral image of a liquid without calibrated light and a second multispectral image of the liquid with calibrated light.

Analyzing multispectral image data of a liquid/beverage to obtain information on the contents of the liquid/beverage may include executing one or more feature detection algorithms, including machine learning algorithms, semantic reasoning techniques, similarity algorithms, and/or other technologies to, among other things, in an automated feature detection, recognize and describe one or more liquid/beverage components that are depicted in a digital image or represented in a spectrum. Some examples of feature detection algorithms that may be used for analyzing multispectral image data include a histogram of oriented gradients (HoG), an edge orientation histogram, a scale-invariant feature transform descriptor (SIFT), and a shape context technique.

For example, the circuitry may be configured to generate spectral difference image data (e.g. a spectral difference image) based on the first multispectral image data and the second multispectral image data.

The circuitry may for example be configured to calculate a reflectance spectrum/image for the object based on spectral information collected from light being reflected from the object, the light originating from the light source. The reflectance, as will also be discussed below, is defined as the fraction of the reflected power of light (intensity) of the incident power of light (intensity). The reflectance spectrum may include information of the reflectance for different wavelengths.

A spectral sensor arrangement may also include a distance sensor and the calculating a reflectance spectrum/image may be based on distance information. For example, as the light source emits a calibrated light spectrum and as the distance between the light source and the object may be known, for instance, since the distance between the depth sensor and the light source is known, it is possible to determine the (exact or nearly) amount of light (power, intensity) at the position of the object, which, in turn, allows to calculate an absolute reflectance spectrum. This is in contrast, for example, to cases where the exact amount of light at the position of the object is not used and where consequently only, for example, a relative reflectance spectrum could be calculated.

The circuitry may be configured to calculate reflectance image data (e.g. a reflectance image) from the spectral difference image.

The circuitry may be configured to determine the reflectance features of the liquid from the reflectance image data.

The circuitry may be further configured to calculate the reflectance spectrum for the object based on spectral information collected from ambient light being reflected from the object. Ambient light cannot be avoided in some embodiments, such that the ambient light can be taken into account for the calculation of the reflectance spectrum.

Correspondingly, the circuitry may be further configured to calculate a difference between the ambient light spectral information being representative of a light spectrum of ambient light being reflected from the object and the calibrated light spectral information being representative of a light spectrum of light originating from the light source and being reflected from the object. Thereby, the influence of the ambient light can be compensated and the (exact or nearly) amount of light (power, intensity) at the position of the object can be determined.

In some embodiments, the circuitry is further configured to drive the light source and the spectral sensor such that the spectral sensor collects first spectral information during an off-state of the light source, where the light source does not emit light, and collects second spectral information during an on-state of the light source, where the light source emits light.

The circuitry may further be configured to calculate a difference between the second spectral information and the first spectral information. Thereby, the influence of the ambient light can be compensated, since by performing the subtraction between the first spectral information and the second spectral information, the (pure) spectral information of the light reflected by the object and origination from the light source can be obtained.

Hence, the circuitry may be further configured to calculate the reflectance spectrum based on the difference between the second spectral information and the first spectral information and the calibrated light spectrum emitted from the light source. Thereby, as discussed, the absolute reflectance spectrum can be obtained.

In an embodiment, in addition to determining multispectral images, the circuitry is configured to determine RGB image data from the spectral difference image data. Determining RGB image data from the spectral difference image data may for example include any algorithm that reduces multispectral image data to RGB image data.

The circuitry may be configured to determine a structural feature or structural features of the liquid from the RGB image data. Determining structural features of the liquid from the RGB image data may include performing a bubble and/or foam analysis. The determining structural features from the RGB image data may for example include feature detection algorithms, including machine learning algorithms, semantic reasoning techniques, similarity algorithms, and/or other technologies to, among other things, in an automated feature detection, recognize and describe one or more liquid/beverage components that are depicted in a digital RGB image. The determining structural features from the RGB image data may also include image matching with RGB images that are prestored in a database.

The circuitry may be further configured to identify a characteristic of the object on the basis of the reflectance spectrum. For example, multiple reflectance spectra being indicative for specific objects, object characteristics, object materials, etc. may be predefined and, for example, stored in a storage, database or the like. By comparing the calculated reflectance spectrum with the predefined reflectance spectra, a reflectance spectrum having the strongest similarity can be identified and the respective characteristics of the object can be identified. The storage may be a hard disk, compact disc, solid state drive, etc. The storage may be included in the mobile reflectometer or it may be accessible via a connection, such as a network connection, wireless connection, the internet, etc.

The circuitry may be configured to determine an analysis result based on the reflectance features and the structural features. For example, the circuitry may combine the results of the reflectance feature analysis obtained from multispectral images with the results of the structural feature analysis obtained from an RGB image.

As an alternative to deriving the RGB image from multispectral images, the circuitry may also be configured to obtain an RGB image of the liquid directly by using e.g. a RGB camera.

In addition to using multi spectral image data and RGB image data, the liquid analysis may also take into account other information captured by sensors such as a temperature sensor, or the like. For example, information about the temperature of the liquid may be obtained by use of a thermometer and a liquid analysis may judge on the quality of the liquid based on the temperature information obtained from the thermometer.

The circuitry may also be configured to generate a query with guidance for asking a user to change image capture settings.

Image capture settings may be anything that has influence on what information a sensor arrangement such as a multispectral camera is capturing. Image capture settings may for example include a position and/or an orientation of a camera, e.g. angles (shooting angle) of a camera such as roll, yaw and pitch. Image capture settings may also include the distance between a liquid/beverage and a camera, and/or the distance between a glass/container and a camera. Still further, image capture settings may also include aspects such as separating an ingredient of a liquid/beverage from the other components/ingredients, or placing a camera closer to a specific component/ingredient of a liquid/beverage.

Generating a query with guidance for asking a user to change image capture settings may for example be implemented by a user interface. The user interface may be associated with visual feedback on a mobile device or may involve voice feedback via a mobile device.

The circuitry may be configured to generate the query with guidance according to insufficient information on the contents of the liquid/beverage. For example, at each step, feedback can be received from a user to achieve more precise information.

The circuitry may be configured to guide the user to change the attitude of a camera (e.g. a shooting angle of a camera) to point to other ingredients of the liquid/beverage.

The circuitry may be configured to guide the user to change the attitude of a camera (e.g. a shooting angle of a camera).

The circuitry may also be configured to guide the user to move a camera and to see a particular object in the liquid/beverage close up.

The circuitry may be configured to generate feedback concerning the liquid/beverage based on the obtained information on the contents of the liquid/beverage. This may for example be done by comparing and matching information about an identified liquid/beverage information of liquids/beverages in a database, or more sophisticatedly by full automatic feedback generation process.

The feedback may for example include ingredients information, nutrition information, and/or allergen information.

The feedback may also include information on the quality of the liquid/beverage. Information about the quality of a liquid/beverage may for example include information about the freshness of a liquid/beverage, its type, its origin, its purity etc.

The circuitry may for example be configured to calculate calories and recommend changes to the generated feedback based on the user's health or diet plan.

The circuitry may be configured to change the feedback generation process based on user feedback. This may allow to improve the precision of feedback generation based on feedback received by the user.

The system may include a sensor arrangement configured to collect multispectral image data of a liquid/beverage. This sensor arrangement may for example be located on a mobile device such as smart phone, tablet, or wearable devices.

Visually liquids/beverages can be characterized first of all by their color, their foam and rising bubbles. The color space human beings perceive covers just tiny and inaccurate information compared to what a spectral device like a spectral sensor may "see". According to some embodiments, it can acquire the complete spectrum and thus allows even distinguishing between liquids/beverages having the same color from a human point of view. Furthermore, chemical components can be derived.

By combining such a spectral analysis with an optical analysis of a liquid/beverage (e.g. of the foam and bubbles of a beer), a judgement of its quality is possible. The optical analysis may include a structure analysis of components of the liquid/beverage (e.g. foam and bubbles) like the structure and amount of foam, sizes of bubbles in the foam or liquid and also the amount of bubbles in the liquid. This may make it possible to judge for the freshness of a liquid/beverage, its type, its origin, its purity etc.

In order to do so several technical realizations are thinkable. In all solutions, three main steps are in common towards the quality analysis. In a first step, there is the data acquisition. After this the acquired data is analyzed and features are derived which are later on used to judge for the quality of the liquid/beverage. Finally, the result is fed back to the user.

The sensor arrangement may for example include a multispectral camera, and/or a spectral imager.

In addition, the sensor arrangement may further include an RGB camera, e.g. in addition to a multispectral camera.

The sensor arrangement may be configured to provide depth information. The sensor arrangement may for example apply stereoscopic imaging, Time-of-Flight imaging (ToF) or other techniques for providing depth information. Accordingly, the circuitry may be configured to use depth information for volume analysis of a whole liquid/beverage or each ingredient of the liquid/beverage to determine the quantity of the ingredients for feedbacks. Depth information may also be helpful to computer vision techniques such as histogram of oriented gradients (HoG), edge orientation histogram, scale-invariant feature transform descriptor (SIFT), and shape context to determined shapes.

The sensor arrangement may be configured to provide mass spectrography information. By utilizing mass spectroscopy data, the circuitry may achieve precise content determination. This may allow identifying various kinds of compounds including sugars, salts, oil, and biomolecules such as proteins. Recent developments in mass spectroscopy have shown that mass spectroscopy can be integrated into a compact equipment such as mobile phones. For example, the aero-thermo-dynamic mass analysis (AMA) described by Kota Shiba & Genki Yoshikawa in Scientific Reports 6, article number 28849 on nature.com can be integrated into various analytical devices, production lines, and consumer mobile platforms. Accordingly, such technology can be beneficially used for liquid/beverage recognition and feedback generation in the context of smart phones.

The sensor arrangement may be configured to provide visible images, infrared images, and/or spectral data.

The circuitry may be configured to employ ingredient/component segmentation on a multispectral image by distinguishing the difference of spectrum properties of ingredients.

The circuitry may be configured to identify ingredients and/or components of the liquid/beverage by analyzing spectrum data.

The circuitry may be configured to use conventional image data (RGB image data) for course identification such as the liquid/beverage name identification. This may help improving the efficiency of processing by narrowing down the candidate liquid/beverage contents. Such conventional image data may for example be compared with reference image data stored in a reference image data base.

According to an embodiment, a system includes circuitry configured to take a first multispectral image of a liquid/beverage without calibrated light; take a second multispectral image of the liquid/beverage with calibrated light; generate a spectral difference image based on the first multispectral image and the second multispectral image; calculate a reflectance image from the spectral difference image; determine reflectance features of the liquid/beverage from the reflectance image; determine an RGB image from the spectral difference image; determine structural features of the liquid/beverage from the RGB image; and determine an analysis result based on the reflectance features and the structural features.

According to another embodiment, a system includes circuitry configured to take a first multispectral image of a liquid/beverage without calibrated light; take a second multispectral image of the liquid/beverage with calibrated light; generate a spectral difference image based on the first multispectral image and the second multispectral image; calculate a reflectance image from the spectral difference image; determine reflectance features of the liquid/beverage from the reflectance image; determine structural features of the liquid/beverage from the reflectance image; and determine an analysis result based on the reflectance features and the structural features.

According to another embodiment, a system includes circuitry configured to obtain a first spectrum of a liquid/beverage without calibrated light; obtain a second spectrum of the liquid/beverage with calibrated light; obtain an RGB image of the liquid/beverage; generate a difference spectrum based on the first spectrum and the second spectrum; calculate a reflectance from the difference spectrum; determine reflectance features of the liquid/beverage from the reflectance; determine structural features of the liquid/beverage from the RGB image; and determine an analysis result based on the reflectance features and the structural features.

From liquid/beverage content determination to feedback generation, the system and/or method of the embodiments may identify the name of a liquid/beverage in front of a camera by utilizing machine learning and refer to existing feedback database based on identified liquid/beverage name to extract the feedback of identified liquid/beverage.

All above described aspects may also be realized as a method or computer program. The method, respectively the computer program may collect information of a liquid/beverage based on multispectral information, depth information and/or mass spectrography information using camera in addition to conventional visible images. The method identifies a liquid/beverage, analyzes liquid/beverage content (e.g. ingredients and/or components), measures volume of ingredients/components, and generates feedback, from collected data. The method may also calculate calories and recommend changes to the generated feedback based on the user's health or diet plan. The method can improve its precision of feedback generation based on feedback received by the user.

The feedback generation can be fully automated with help of an intelligent identification system. The method can determine the volume of ingredients, the quantity of salt, sugar and oil based on measured data. The system may also calculate calories and recommend changes to the generated feedback based on a user's health or diet plan.

The embodiments described below disclose a method to identify a liquid/beverage by taking a visual image, multispectral information, depth information and/or mass spectrography information using a camera. The measured data is analyzed to identify a liquid/beverage and the ingredients of a liquid/beverage. The proposed disclosure also provides a system including a bot agent that iteratively provides feedback associated with capturing the images to a user for precisely identifying a liquid/beverage (for example, tipping a glass, dipping foam, etc.). The system generates a feedback upon identifying the liquid/beverage. The system may also calculate calories and recommend changes to the generated feedback based on the user's health or diet plan.

The embodiments described below in more detail may allow an end-consumer to do an immediate analysis to get a liquid/beverage's chemical composition. This may allow him to conclude for allergens, toxics or the quality as such.

In particular, the embodiments described below may allow an end-consumer to analyze liquids/beverages without taking a sample of the relying liquid and providing it to a laboratory, which is time consuming and expensive.

By combining methods of Computational Photography with Spectral Sensing a compact device can be realized which can be integrated in already existing wearables and provide an additional functionality which overcomes the current existing limitations in doing an on-side and instantaneous quality inspection of liquids/beverages or liquids as such.

By combining methods of Computational Photography with Spectral Sensing such limitations can be overcome and it is possible to build a compact and small device which can be integrated in any portable or mobile unit and thus allows an on-site and instantaneous analysis of liquids/beverages or other kind of liquids for their quality.

In the embodiments described below, beverage analysis is described. However, all embodiments may likewise be used in the general context of liquid analysis, e.g. medical infusions can be analyzed in the same way as described below with regard to beverages.

System for Beverage Analysis

FIG. 1 schematically describes an embodiment of a system for beverage analysis. The system for beverage analysis is composed of a sensor arrangement 14, a processor 15, and a user interface 13. The sensor arrangement 14, according to this example, is supposed to be on a mobile device such as a smart phone, a tablet or a wearable device. The processor 15 is also located on a mobile device. However, according to other embodiments, the processor 15 may also be located in part or as a whole on a remote workstation or cloud server. The user interface 13 may be associated with visual feedback, e.g. on a mobile device or the voice feedback via a mobile device.

Feedback Generation

Figure 2:
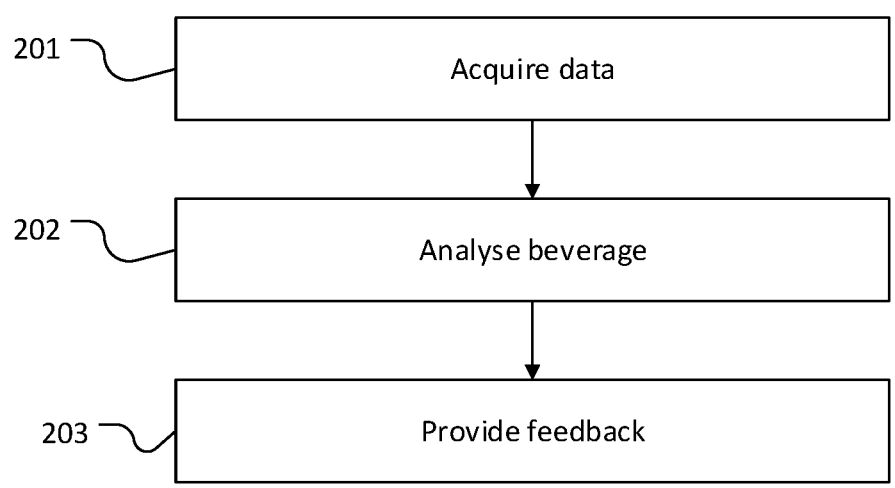
FIG. 2 describes an example of a feedback generation process.

FIG. 2 describes an example of a feedback generation process. At 201, data from a beverage is acquired (e.g. by means of sensor arrangement 14 in FIG. 1). The data, according to this embodiment, is comprised of multispectral images captured by a multispectral sensor, but it can be various kinds of information associated with various devices, such as visible images, infrared images, spectral data and depth information. At 202, information about the beverage, e.g. the chemical content, is determined by analyzing measured data by utilizing computer vision techniques. For instance, based on given multispectral images, ingredient segmentation is employed by distinguishing the difference of spectrum properties of ingredients. Also, ingredients can be identified by analyzing spectrum data. Depth information may be used for volume analysis of a whole beverage or each ingredient to determine the quantity of the ingredients. Mass spectroscopy data may be utilized to achieve precise content determination. This allows identifying various kinds of compounds including sugars, salts, oil, and biomolecules such as proteins. Conventional image data can be used for course identification such as the beverage name identification (e.g. "beer"). This may help improving the efficiency of processing by narrowing down the candidate beverage contents. Finally, at 203, feedback concerning the beverage is generated. This can be done by comparing and matching the beverage content of an identified beverage with those of beverages on an existing beverage database, or more sophisticatedly, by a full automatic content analysis process. From beverage content determination, the method may for example identify the beverage name by utilizing machine learning and refer to an existing beverage database based on the identified beverage name to retrieve the contents of an identified beverage from the beverage database. Providing feedback concerning a beverage may in particular include providing information about the quality of the beverage.

Beverage Analysis Process

Figure 3:
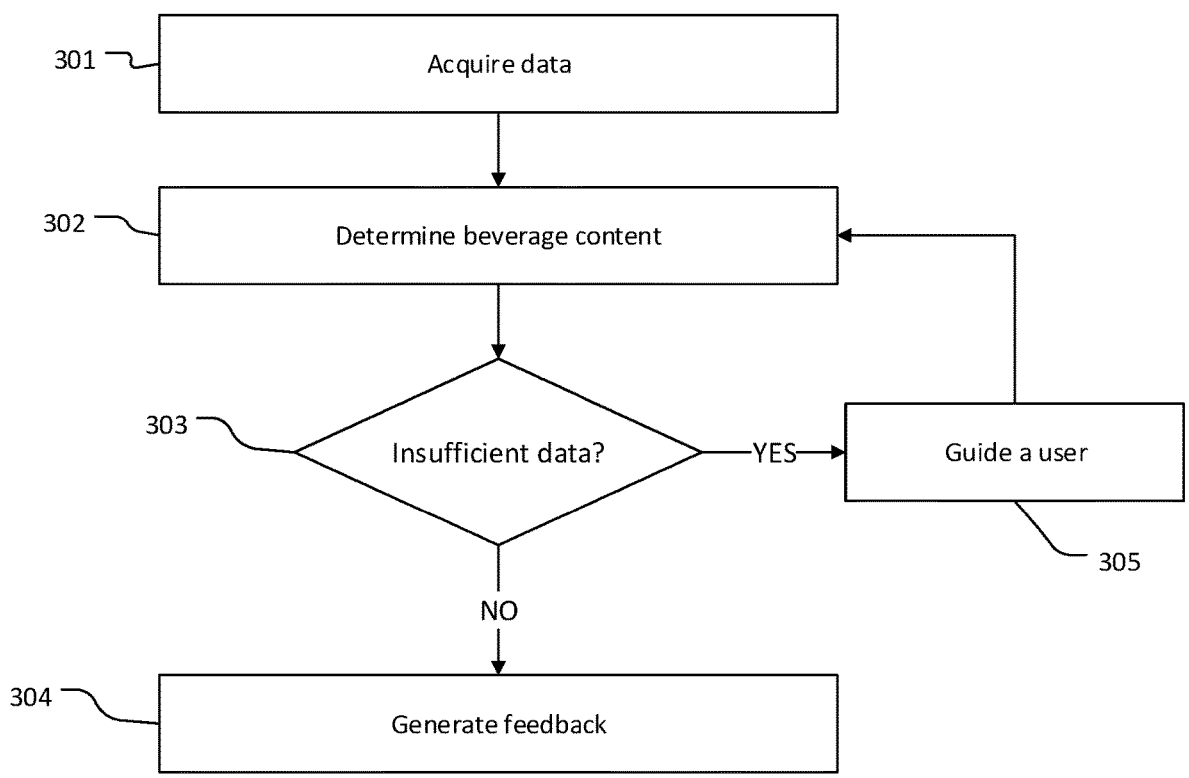
FIG. 3 shows an embodiment of a beverage analysis process associated with user feedback.

FIG. 3 shows an embodiment of a beverage analysis process associated with user feedback. As in the example of FIG. 2, at 301, data from a beverage is acquired, e.g. by means of sensor arrangement 14 in FIG. 1. At 302, information about the beverage, e.g. the chemical content, is determined by analyzing measured data by utilizing computer vision techniques. At 303, it is determined if there is sufficient data for generating feedback concerning the beverage. If it is decided at 303 that there is sufficient data for providing feedback concerning the beverage, the process continues at 304. At 304, feedback is generated concerning the beverage based on the determined beverage content. If it is decided at 303 that there is insufficient data for generating feedback concerning the beverage, the process continues at 305. At 305, the process generates a query to guide a user to provide more information on the beverage. This process may be repeated iteratively until the whole beverage content has been determined or until the identification of the beverage can be performed or until a predetermined number of the candidate beverages can be identified. At each step, feedback can be received from a user to achieve a more precise beverage analysis. For example, if the process cannot decide the beverage content since the available data is not sufficient, or the data includes some ambiguities, the system can iteratively guide a user to check the beverage to identify the content precisely or to provide better feedback concerning the beverage (e.g. by instructing the user to first direct a sensor/camera at the foam area of a beer and then to direct the sensor/camera at the liquid area of the beer).

It should be noted that not necessarily the whole chemical content and/or ingredients must be determined to identify a beverage. According to some embodiments, the chemical content and/or ingredients of a beverage are identified up to a predetermined level at which an identification of the beverage can be performed. If the beverage can be fully identified based on only parts of its chemical content and/or ingredients, then a reference database may be queried to receive the remaining content of the beverage that have not yet been identified. It also should be noted that the user may select one beverage from the identified candidates displayed on a display of the mobile device. The selection may be used to update the database of the liquids and to improve the machine learning.

The guidance may be generated according to the insufficient data. Exemplifying relationship between insuffidata and respective guidance is given in the embodiments described below with reference to FIGS. 4, 5a, and 5b.

Figure 4:
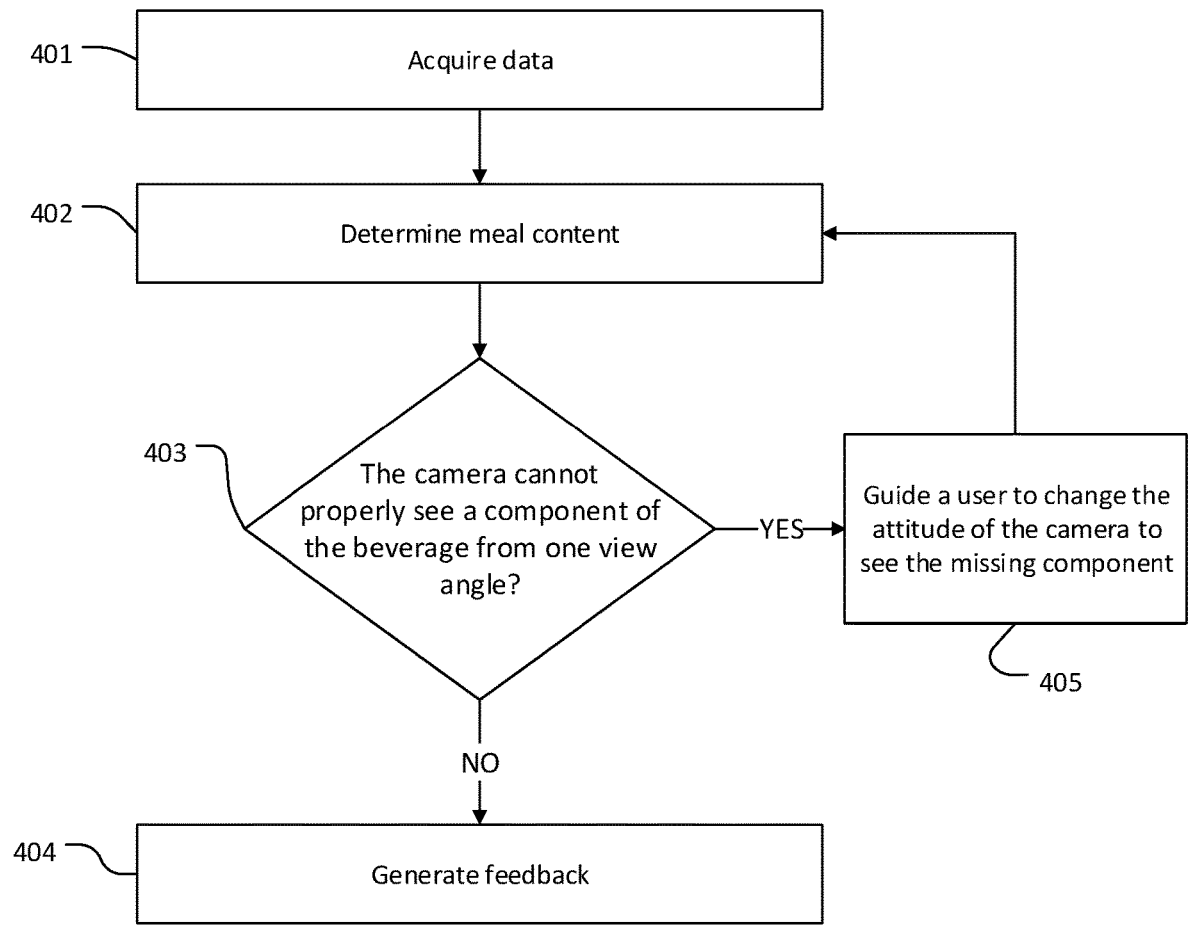
FIG. 4 shows a specific embodiment of a feedback generation process associated with user feedback.

FIG. 4 shows a specific embodiment of a beverage analysis process associated with user feedback. At 401, data from a beverage is acquired, e.g. by a multispectral camera that is integrated in a mobile phone. At 402, information about the beverage, e.g. the beverage content, is determined by analyzing measured data by utilizing computer vision techniques. At 403, it is determined if the camera cannot properly see a component of the beverage from one view angle. If it is decided at 403 that the camera can properly see all components of the beverage from one view angle, the process continues at 404. At 404, feedback is generated for the beverage based on the determined beverage content. If it is decided at 403 that the camera cannot properly see a component of the beverage from one view angle, the process continues at 405. At 405, the process generates a query to guide a user to change the attitude of the camera to see the missing component. Changing the attitude may for example include changing the position and/or orientation (shooting angle) of the camera. This process may be repeated iteratively until the whole beverage content has been determined. This process may be particularly helpful if there is not enough spectral information available from one viewing angle.

User Queries

Figure 5A:
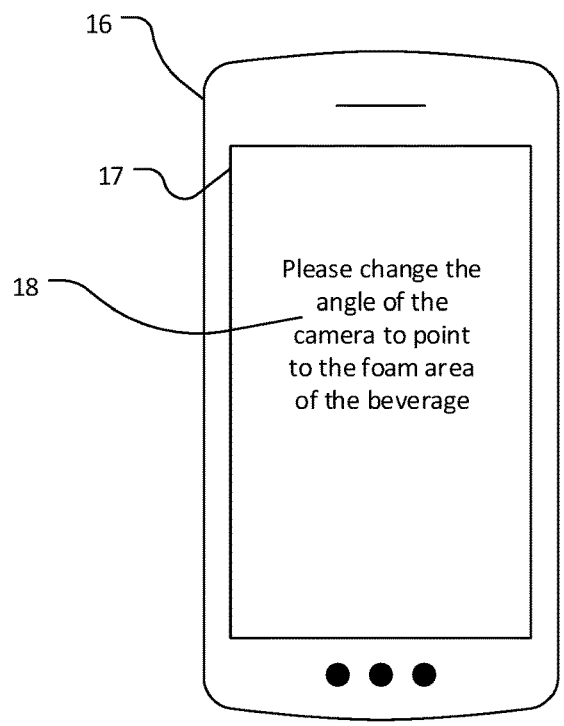
FIG. 5a shows an embodiment of a user query on a display of a mobile phone.

FIG. 5a shows an embodiment of a user query on a display of a mobile phone. The mobile phone 16 is equipped with a multispectral camera (e.g. on the back side of the device, thus not shown in FIG. 5) that is configured to analyze multispectral image data of a beverage to obtain information on the contents of the beverage. The mobile phone 16 includes a display screen 17 that acts as user interface. The display screen 17 shows a query 18 to guide a user to change the attitude of the camera to point to the foam area of the beverage. A user having read this query 18 can react by changing the attitude of the camera, e.g. the shooting angle of the camera (or the angle of the mobile phone) to point to the foam area of the beverage. The process can then repeat determining information about the beverage by analyzing measured data, now based on the changed angle of the camera. This may reveal better information on the beverage, e.g. more data about the foam of the beverage may allow to provide better feedback on the quality of the beverage.

Figure 5B:
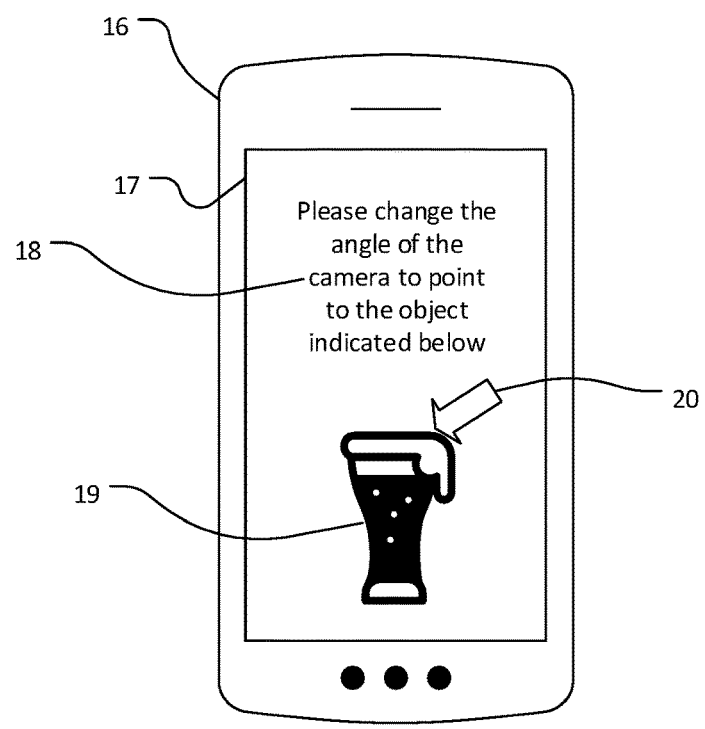
FIG. 5b shows an alternative embodiment of a user query on a display of a mobile phone.

FIG. 5b shows an alternative embodiment of a user query on a display of a mobile phone. According to this embodiment, the mobile phone 16 displays an image 19 of a beverage as captured by the camera. Further, the mobile phone 16 displays a query 18 that guides a user to change the attitude of the camera to point to the component of the beverage as indicated by an arrow 20 on the image 19. A user having read this query 18 can react by changing the attitude of the camera, e.g. the shooting angle of the camera (or the angle of the mobile phone) to point to the component identified by the arrow 20. The process can then repeat determining information about the beverage by analyzing measured data, now based on the changed angle of the camera.

Beverage Analysis by Means of Reflectance Features

Figure 6:
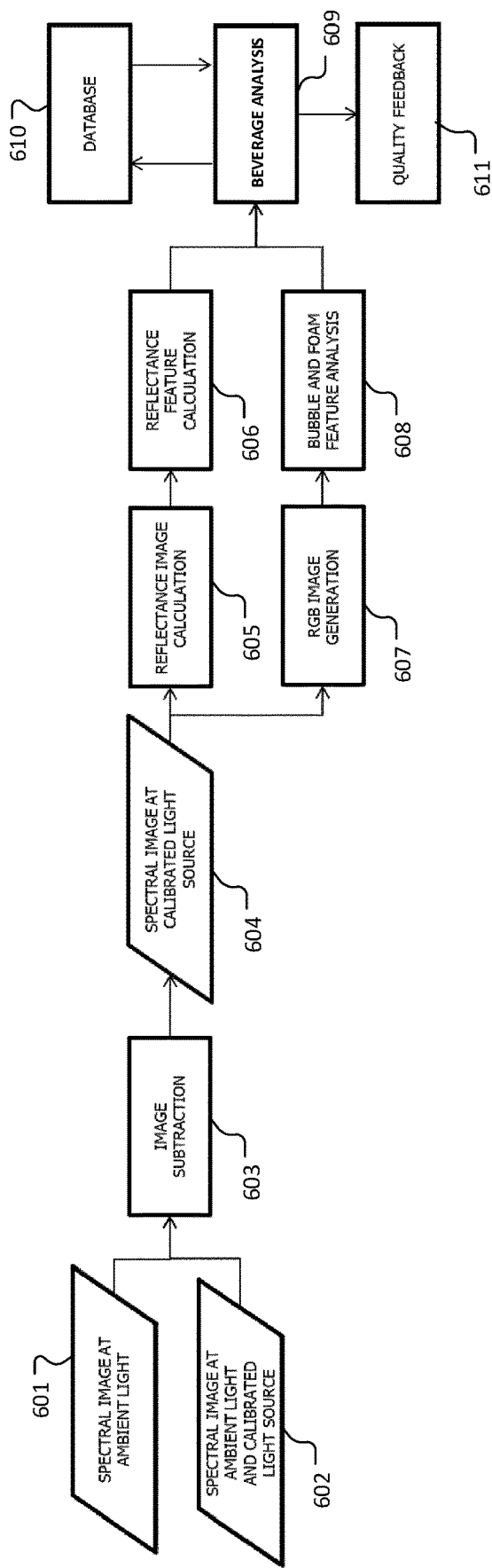
FIG. 6 shows an embodiment of a method for beverage analysis.

FIG. 6 shows an embodiment of a method for beverage analysis in more detail. According to this embodiment, a spectral imager (e.g. spectral sensor) and a calibrated light source is utilized. By illuminating a beverage first without calibrated light source (that is, by e.g. ambient light) a spectral image 601 is taken. Afterwards, a second spectral image 602 is taken with calibrated light source. At 603, a spectral image 604 is generated by subtraction which corresponds to the condition if only light of the calibrated light source is present. From this, at 605, a reflectance image is calculated. From this reflectance image, at 606, by preprocessing steps reflectance features (like ratios or differences between different wavelengths) are derived. Simultaneously, at 607, an RGB image is derived from the spectral image 604. From this RGB image, at 608, foam and bubbles if present are analyzed and respective features like the size of bubbles or bubble density in the liquid or within the foam are derived. At 609, based on the combined features, reflectance, foam and bubbles, the beverage analysis is accomplished. This process might take into account an additional database 610 containing further information about the identified or classified beverages and its components. Optionally also information from the bottle's label can be involved here. At 611, the results of the beverage analysis are output as quality feedback.

It should be noted that the creation of an RGB as done at 607 in the process of FIG. 6 is not necessarily required as the spectral image itself could be used directly for a foam and bubble analysis.

Figure 7:
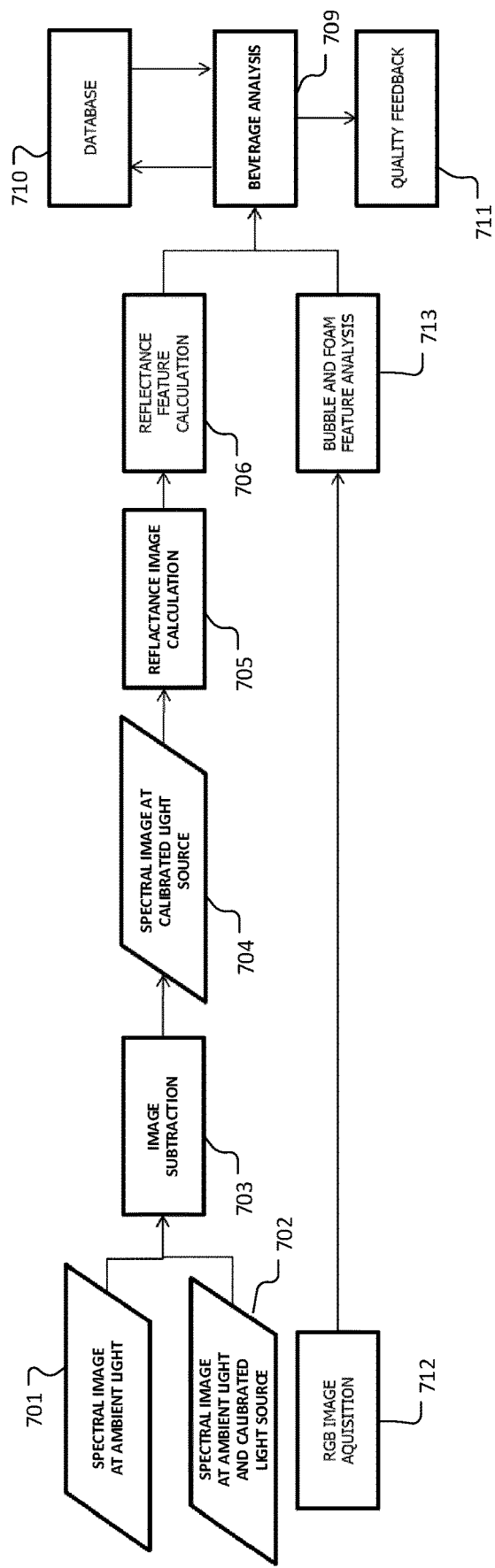
FIG. 7 shows another embodiment of a method for beverage analysis.

FIG. 7 shows another embodiment of a method for beverage analysis. According to this embodiment, a miniaturized spectrometer, RGB imager and a calibrated light source is utilized. By illuminating a beverage first without calibrated light source a spectral image 701 is taken. Afterwards, a second spectral image 702 is taken with calibrated light source. At 703, a spectral image 704 is generated by subtraction which corresponds to the condition if only light of the calibrated light source is present. From this spectral image 704, at 705, a reflectance image is calculated. From this reflectance image, at 706, by preprocessing steps, reflectance features are derived. Simultaneously, at 712, an RGB image is taken with RGB imager under ambient light conditions. As in the embodiment of FIG. 6, the RGB image allows, at 713, analyzing foam and bubbles if present and deriving respective features. Based on the combined features, reflectance, foam and bubbles, at 709, the beverage analysis is accomplished. Again, this step might take into account an additional database 710 containing further information about identified or classified beverages and its components. At 711, the results of the beverage analysis are output as quality feedback.

Generating Spectral Reflectance Images

Figure 8A:
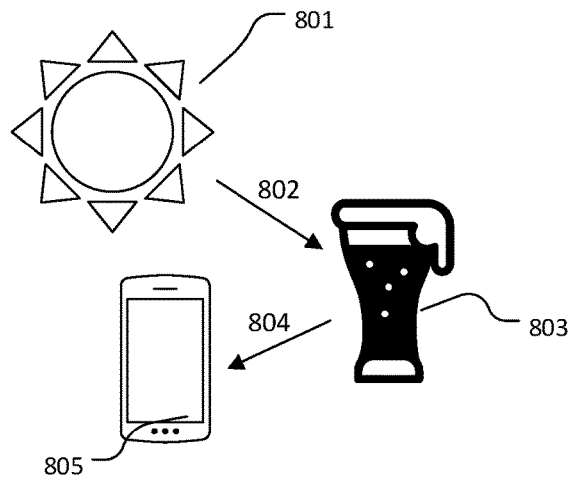
FIG. 8a schematically describes a process of generating a spectral reflectance image using ambient light.

FIG. 8a schematically describes a process of generating a spectral reflectance image using ambient light. Ambient light 802 (from a light source 801 such as the sun or lamps inside a building) illuminates a beverage 803. The ambient light 802 is reflected on the beverage 803 to produce reflected light 804. The reflected light 804 is captured by a multispectral camera or a spectrometer mounted on a smart phone 805. This process generates a spectral image at ambient light such as 601 in the embodiment of FIG. 6, or, respectively, a spectrum at ambient light such as 701 in the embodiment of FIG. 6.

Figure 8B:
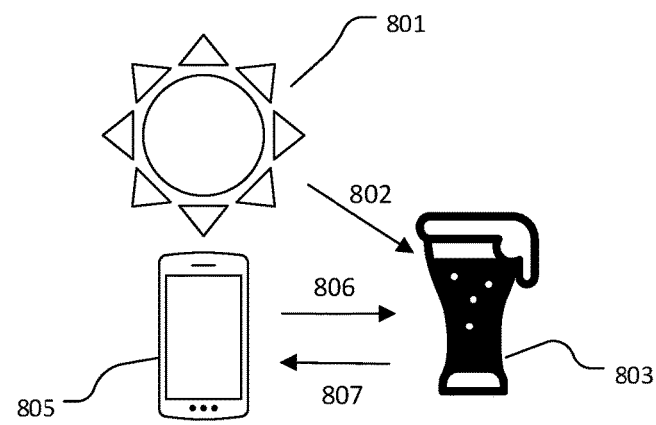
FIG. 8b schematically describes a process of generating a spectral reflectance image using a calibrated light source.

FIG. 8b schematically describes a process of generating a spectral reflectance image using a calibrated light source. Ambient light 802 (from a light source 801 such as the sun or lamps inside a building) illuminates a beverage 803. In addition, light 806 from a calibrated light source (e.g. sunlight or light from lamps) mounted on a smart phone 805 illuminates a beverage 803. The ambient light 802 and the calibrated light 806 is reflected on the beverage 803 to produce reflected light 807. The reflected light 807 is captured by a multispectral camera or a spectrometer mounted on a smart phone 805. This process generates a spectral image at ambient light and calibrated light such as 602 in the embodiment of FIG. 6, or, respectively, a spectrum at ambient light and calibrated light such as 702 in the embodiment of FIG. 6.

Figure 8C:
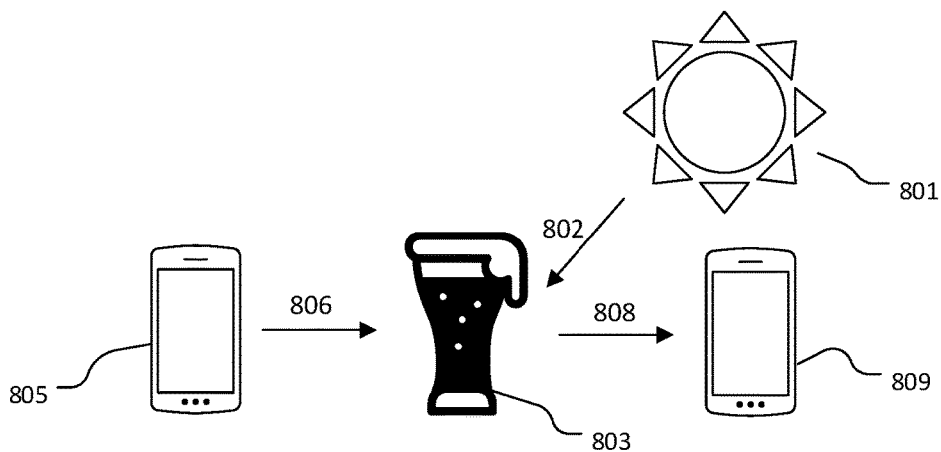
FIG. 8c schematically describes a process of generating a spectral image using calibrated light and transmission spectroscopy.

FIG. 8c schematically describes a process of generating a spectral image using calibrated light and transmission spectroscopy. Ambient light 802 (from a light source 801 such as the sun or lamps inside a building) illuminates a beverage 803. In addition, light 806 from a calibrated light source (e.g. sunlight or light from lamps) mounted on a first smart phone 805 illuminates a beverage 803. The ambient light 802 is reflected on the beverage 803 and, together with calibrated light that is transmitted through the beverage 803, produces light 808 that is captured by a multispectral camera or a spectrometer mounted on a second smart phone 809. This process generates a spectral image at ambient light and calibrated light, or, respectively, a spectrum at ambient light and calibrated light using transmission spectroscopy. Smartphones 805 and 809 are communicatively coupled via a radio connection (Bluetooth, WLAN, or the like) so that smartphone 809 can be informed about the specifics of the calibrated light source of smartphone 805, either directly or via a server or cloud component. Such a communication path can also be used to synchronize the process of image/spectrum capturing with the process of calibrated light generation between smartphone 805 and smartphone 809.

In the embodiments described above it is foreseen that the spectral imager and/or the calibrated light source are mounted on mobile devices such as a smartphone or a smart watch. However, according to other embodiment, is also possible that the spectrometer or spectral imager (together with the calibrated light source) is mounted in the bottom of a cup, it's coaster or a glass a consumer has at home. Embodiments may thus be based on mobile devices, smartphones, tablets, smartwatches, glasses or other kind of wearables. Still further, embodiments may be based on cups, tumblers or mugs or the like.

FIG. 8d shows an embodiment in which the spectral imager and/or the calibrated light source is implemented in a kitchen appliance, here a coffee machine, to monitor the quality of the foam of the coffee. The concepts of the embodiments described above may also be applied in this case. In addition, the results of the foam quality monitoring can be utilized to provide an alert to a user of the machine. Such an alert may indicate to the user the necessity of a maintenance of the machine, or it may send information relating to the machine condition to a remote server automatically to request a maintenance check of the machine. In yet other embodiments, machine settings are changed for preparation of the coffee in accordance with the results of the foam analysis. The same principles may be applied in other appliances such as in a beer creating machine to analyze beer foam quality.

Further, according to yet other embodiments, it is also possible to do the imaging from different point of views and use the angle dependent reflectance measurement as additional or supporting criteria for doing the beverage analyzing and quality judgement.

In yet other embodiments, a calibration measurement is performed to determine the influence of the glass thickness on to the reflectance measurement.

The embodiments described here allow an on-site and instantaneous analysis of beverages.

Reflectance Measurements

Figure 9A:
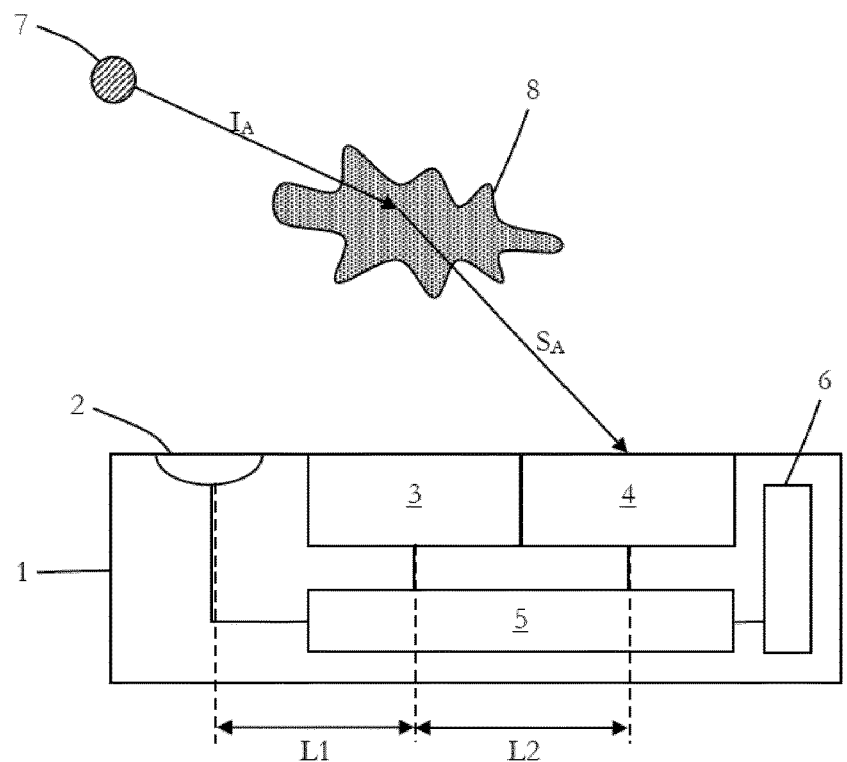
FIG. 9a illustrates a first measurement for obtaining a reflectance spectrum, wherein the light source of the mobile reflectometer is switched off.
Figure 9B:
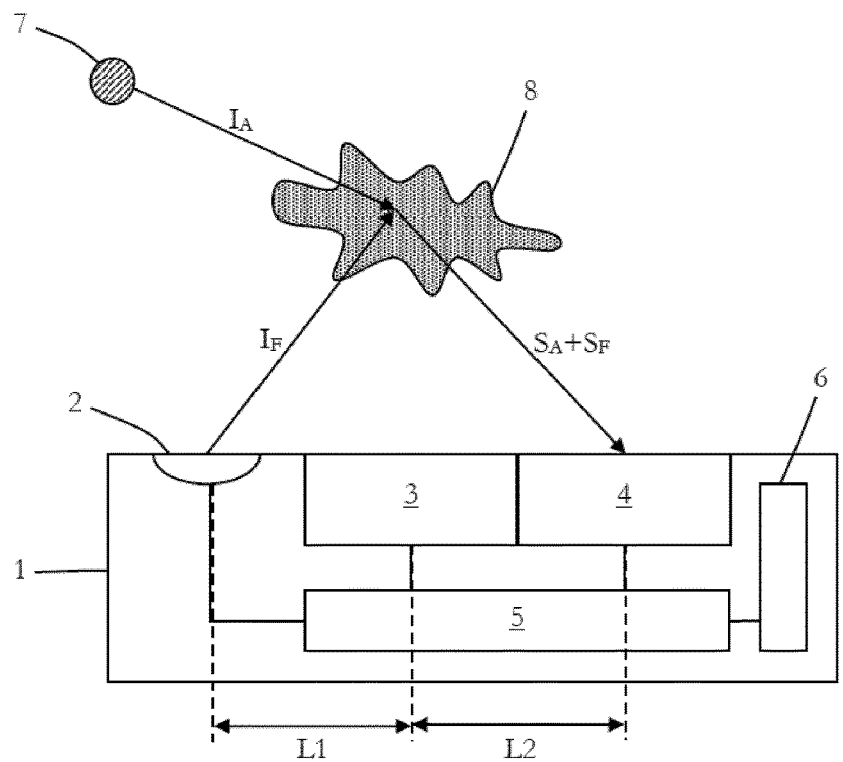

In the following, the measurement of the reflectance of a liquid according to an embodiment is described. In this embodiment, the measurement of the reflectance for the object, here a liquid, is done by performing two spectral measurements, wherein FIG. 9a illustrates a first measurement and FIG. 9b illustrates a second measurement.

A first measurement takes place (FIG. 9a), when the light source is switched off, e.g. by the processor 5, such that only light from an ambient light source 7, such as the sun or other light source, is present.

Then, the processor drives the spectral sensor 4 accordingly to collect first spectral information about light which is reflected by the object 8 in the form of a spectral image or a spectrum $S_A$ and which incidents into the spectral sensor 4. The spectrum $S_A$ can be stored in a memory, storage or the like of the reflectometer 1.

For the second measurement, the calibrated light source 2 is switched on, e.g. by the processor 5. Now, ambient light emitted from the ambient light source 7 and light from the calibrated light source 2 illuminate the object of interest. The spectral sensor 4 collects second spectral information in the form of a spectral image or a spectrum $S_{A+F}$ for the light reflected from the object 8 origination from the calibrated light source 2 and the ambient light source 7. Hence, the reflected light includes light from the ambient light source 7 and light from the calibrated light source 2.

Additionally, at the same time of the second measurement and the same time as the spectral sensor 4 is driven by the processor 5, the processor 5 also drives the depth sensor 3 which determines a distance between the depth sensor 3 and the object 8 by capturing a depth map D. It is assumed that the relative distance between object 8 and reflectometer 1 is the same in both measurements. Of course, the point of time of driving the depth sensor 3 is only exemplary, and, in principle, the depth sensor 3 can be driven at any point of time for obtaining the depth map D.

The spectra $S_A$ and $S_{A+F}$, the depth map D and other parameters may be stored by the processor 5 in a memory, storage or the like.

Figure 10:
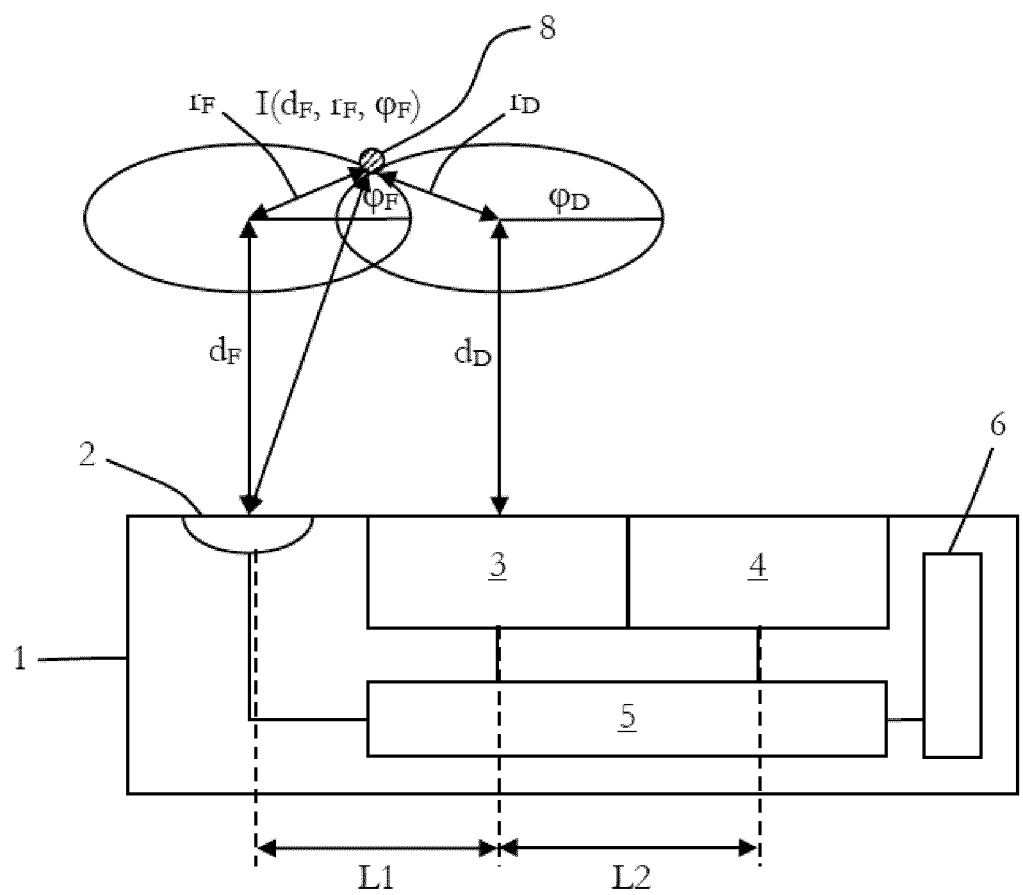
FIG. 10 illustrates a coordinate transformation.

After having performed the two measurements, the processor 5 calculates the absolute reflectance spectrum, as follows and as also illustrated in FIG. 10:

First, a spectrum $S_F$ is calculated, which represents light intensities reflected from the object 8 as if only light were reflected from the object 8 originating from the light source 2. This is done by subtracting the spectrum $S_{A+F}$ obtained during the second measurement where the light source 2 was switched on and the spectrum $S_A$ obtained in the first measurement where the light source 2 was switched off from each other:

$$S_F = S_{A+F} - S_A$$

Second, the absolute power $I_F$ of the calibrated light source 2 at the position of the object 8 is calculated by the processor 5.

In the coordinate system of the depth sensor 3 the object 8 is located at $(d_D, r_D, \varphi_D)$, see also FIG. 10. This can be directly derived from the acquired depth map D which includes the information of the distance of the object 8 with respect to the depth sensor 3.

The processor 5 performs a simple coordinate transformation T, which results in the coordinates $(d_F, r_F, \varphi_F)$ in the coordinate system of the calibrated light source 2:

$$(d_F, r_F, \varphi_F)^T = T*(d_D, r_D, \varphi_D)^T$$

These coordinates $(d_F, r_F, \varphi_F)$ can be used for calculating the absolute incident power $I_F$, as introduced before:

$$I_F = I(d_F, r_F, \varphi_F).$$

Finally, the absolute reflectance R is obtained by dividing the reflected power $S_F$ with the incident power $I_F$:

$R = S_F/I_F$

As mentioned above, in the present embodiment the depth sensor 3 and the spectral sensor 4 are very close to each other such that the influence of the distance between them is negligible. In other embodiments, the distance between the depth sensor 3 and the spectral sensor 4 can be considered by performing another coordinate transformation, for example, into the coordinate system of the spectral sensor 4. However, then the classical parallax problems, such as occlusion, may arise.

In the present embodiment, the calculation was done for a single point of an object. In other embodiments, the depth sensor and/or the spectral sensor may be two-dimensional (2D) sensors such that also a complete 2D reflectance measure may be performed in such embodiments. Moreover, the single point measurement as done in the embodiment discussed above can also be repeated for multiple points of an object.

Kitchen Appliance

Figure 11:
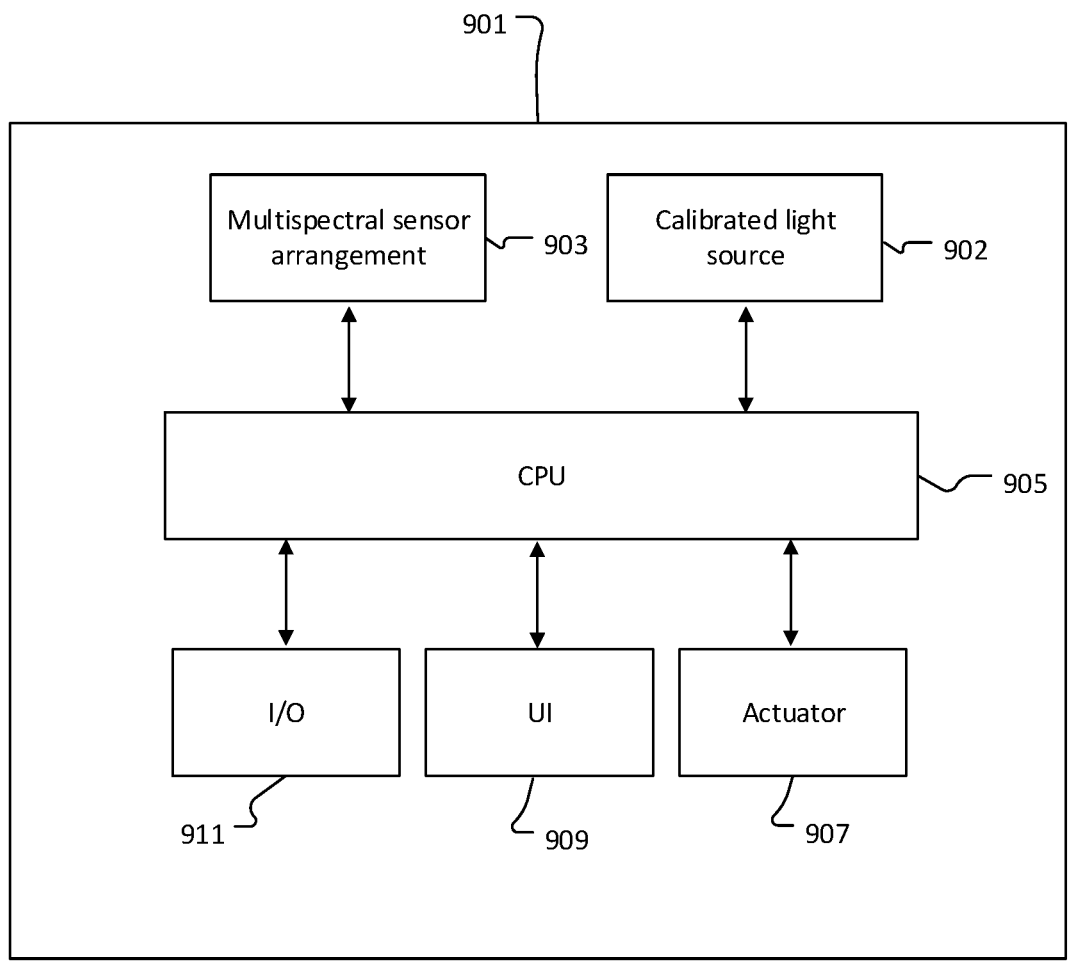
FIG. 11 shows an embodiment in which the spectral imager and/or the calibrated light source is implemented in a kitchen appliance.

FIG. 11 shows a schematic representation of components of a liquid processing machine such as a kitchen appliance that is based on liquid analysis. According to an embodiment, the liquid processing machine is a coffee machine. The coffee machine 901 includes a calibrated light source 902, a multispectral sensor arrangement 903, a processor 905, an actuator 907, a user interface 909, and a network interface 911. A user of the coffee machine 900 may start a process of coffee brewing by means of user interface 909. The multispectral sensor arrangement 903 is arranged inside the coffee machine to capture multispectral images of the freshly brewed coffee using calibrated light of calibrated light source 902. The processor 905 is configured to determine reflectance features and/or structural features (e.g. foam) as described with regard to the embodiments of FIG. 6 or 7, and to perform a liquid/beverage analysis based on an analysis of these reflectance features and/or structural features (e.g. a foam analysis). From this analysis, the coffee machine 901 receives information about the quality of the coffee. Based on this information about the quality of the coffee, the coffee machine 900 determines whether or not modifications to the process of brewing coffee should be made. For example, the processor 905 may determine that the freshly brewed coffee is too strong and may thus decide, that the brewing process should be modified continued by controlling actuator 907 to add more water. In addition or alternatively, the processor may decide that changes to the presettings of the coffee machine should be made based on the analysis result. In addition or alternatively, the processor may decide that the coffee brewing process does not work in a proper way and may decide to electronically contact the maintenance service of the coffee machine, e.g. by automatically sending a message or an Email to the maintenance service via network interface 911.

Displaying Feedback

Figure 12A:
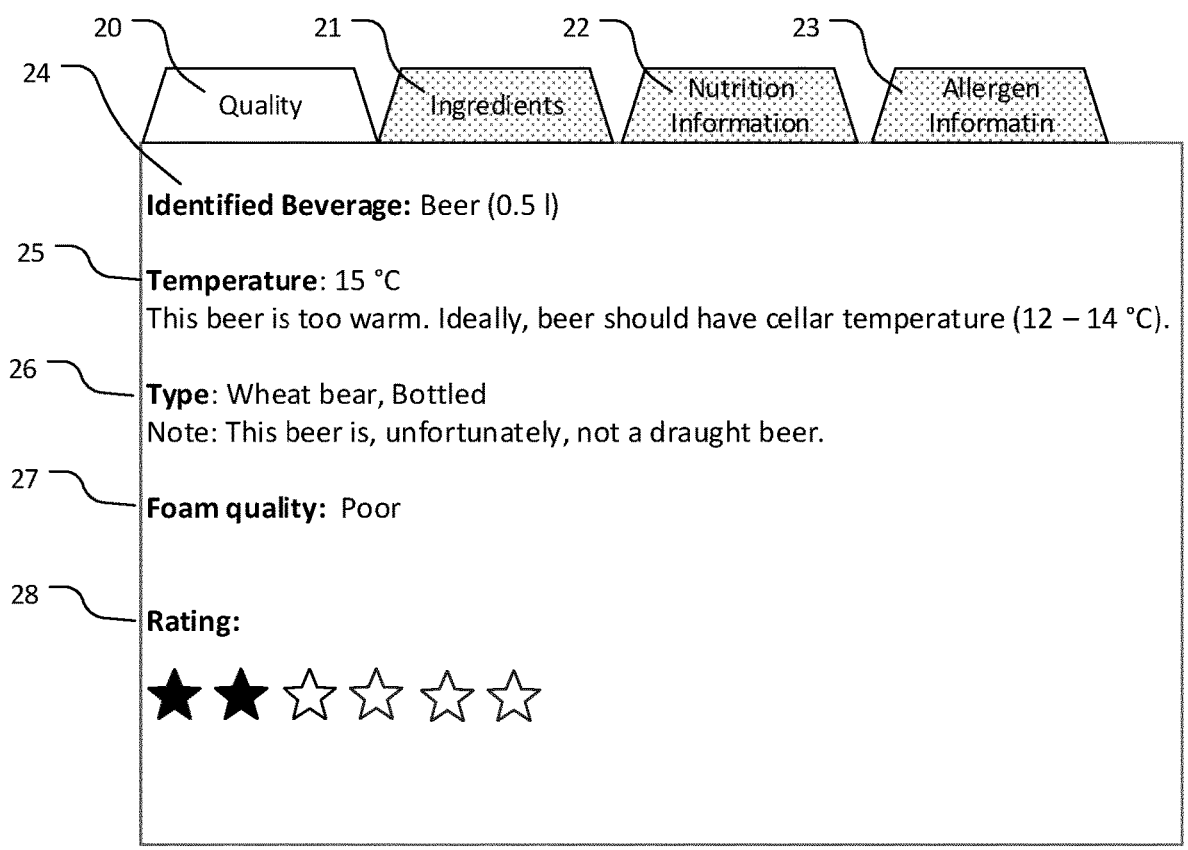
FIGS. 12a,b,c d show an example of generated feedback concerning for a beverage.

FIGS. 12a,b,c,d show an example of generated feedback for a beverage.

FIG. 12a shows feedback as it may be displayed on the screen of a mobile device. The feedback includes four subsections, "Quality" 20, "Ingredients" 21, "Nutrition information" 22 and "Allergen information" 23.

In FIG. 12a, the "Quality" section 20 is selected and displayed. In this section 20, information and notes concerning the quality of the beverage are provided. At 24, the name of the identified beverage is displayed, here "Beer". At 25, the temperature of the beverage is displayed. In the embodiment, it is indicated that the beverage has a temperature of 15° C. This temperature indication is accompanied by a note that states "This beer is too warm. Ideally, beer should have cellar temperature (12-14° C.)". At 26, information concerning the type of the beverage is provided. In the embodiment, it is indicated that the beverage is a "Wheat beer" and that it is a bottled bear. This type information is accompanied by a note that states "This beer is, unfortunately, not a draught beet". At 27, information concerning the foam quality of the beverage is provided. In the embodiment, it is indicated that the foam quality is "Poor". At 28, an overall rating of the beverage quality is provided in visual form. In the embodiment, it is indicated that the overall quality of the beverage is two out of six stars, where six stars of six starts would indicate optimal quality and zero stars of six starts would indicate the worst quality.

According to other embodiments, the quality feedback may also include information about e.g. chemical components, age, origin, etc. of the beverage under analysis.

Figure 12B:
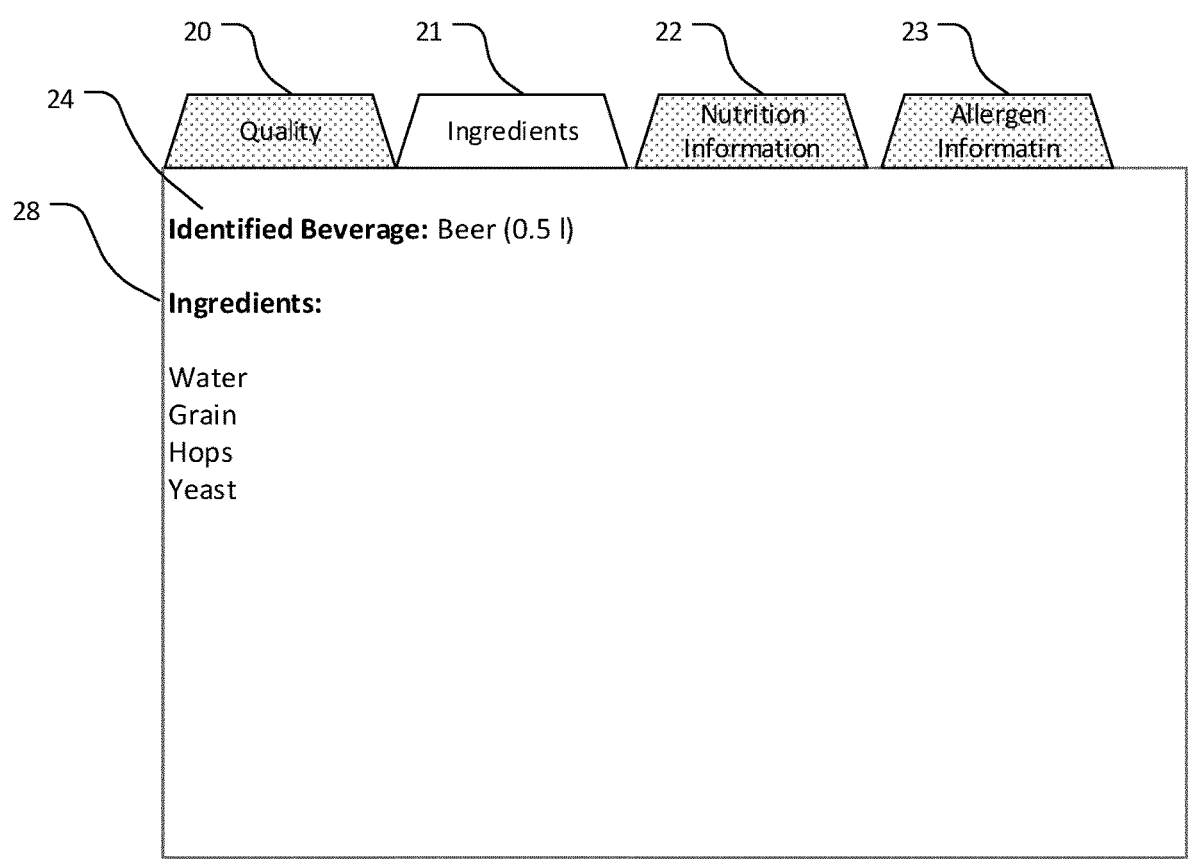

In FIG. 12b, the "Ingredients" section 21 is selected and displayed. At 24, the name of the identified beverage is displayed, here "Beer". At 28, the ingredients of the beverage are identified. In the embodiment, a beer with the ingredients water, grain, hops and yeast has been identified.

Figure 12C:
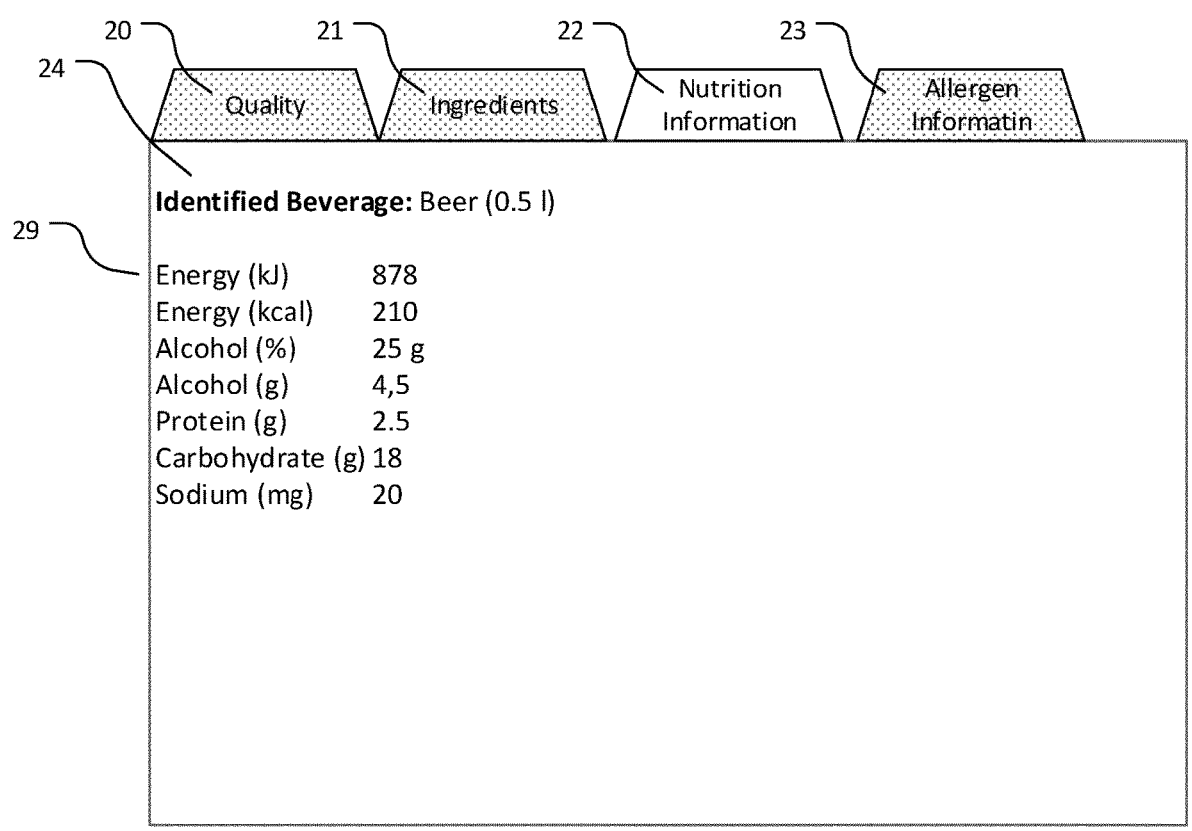

In FIG. 12c, the "Nutrition information" section 22 is selected and displayed. At 29, the nutrition information of the beer is identified. In the embodiment, the beer is identified as including 878 kJ energy (which is 210 kcal), 25 g alcohol (which is 0.05 volume %), 2.5 g protein, 18 g Carbohydrate, and 20 mg sodium.

Figure 12D:
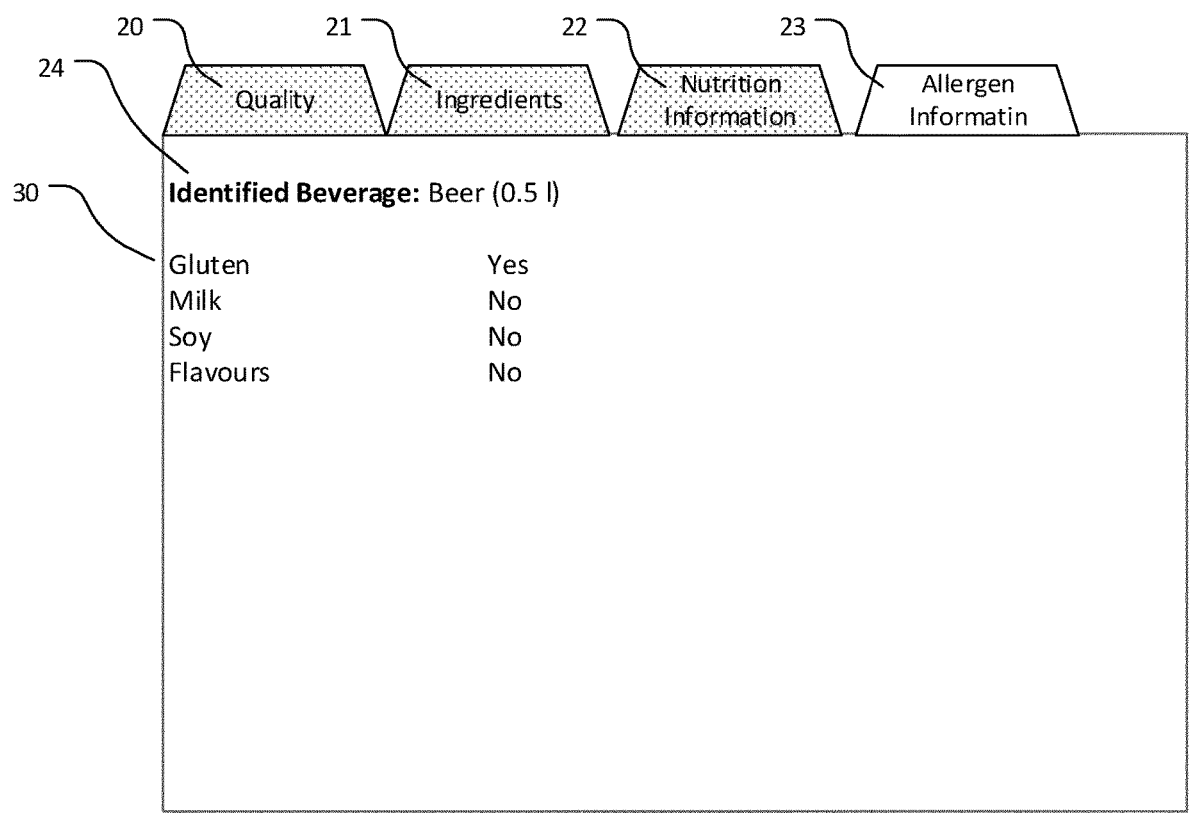

In FIG. 12d, the "Allergen Information" section 23 is selected and displayed. At 30, the allergen information of the beverage is identified. In the embodiment, the beverage is identified as including gluten as potential allergen. The system may also provide allergen warnings based on pre-stored information about allergies of a user.

The feedback generation can be fully automated with the help of the above-described intelligent identification system. The method can determine the quantity of ingredients, e.g. the quantity of salt, and/or sugar and oil based on measured data. The system may also calculate calories and recommend comments based on a user's health or diet plan.

System for Feedback Generation via Internet

Figure 13:
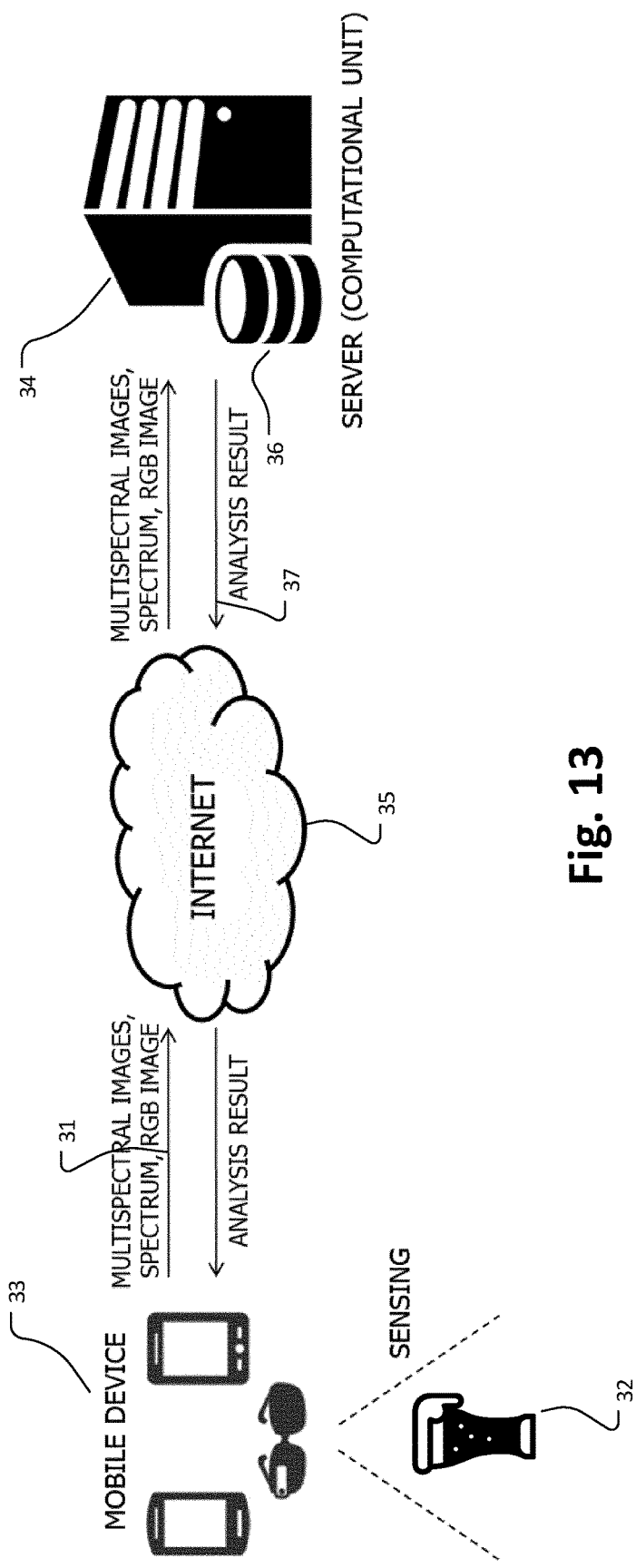
FIG. 13 schematically describes an embodiment of a system for feedback generation via Internet.

FIG. 13 schematically describes an embodiment of a system for feedback generation via Internet. The system generates an analysis result 37 as feedback by visual observation. Multispectral images, a spectrum, and/or an RGB image 31 of a beverage 32 are captured by a multispectral imaging device, by a spectral imager or, respectively, by a RGB camera mounted on a smart device 33. The measured data 31 is transferred to computational unit 34 via the Internet 35. On the computational unit 34, an analysis result 37 is determined by machine learning based on the measured data 31 referring to existing beverage databases 36. The analysis result 37 can be composed of several feedback options shown to a user.

Figure 14:
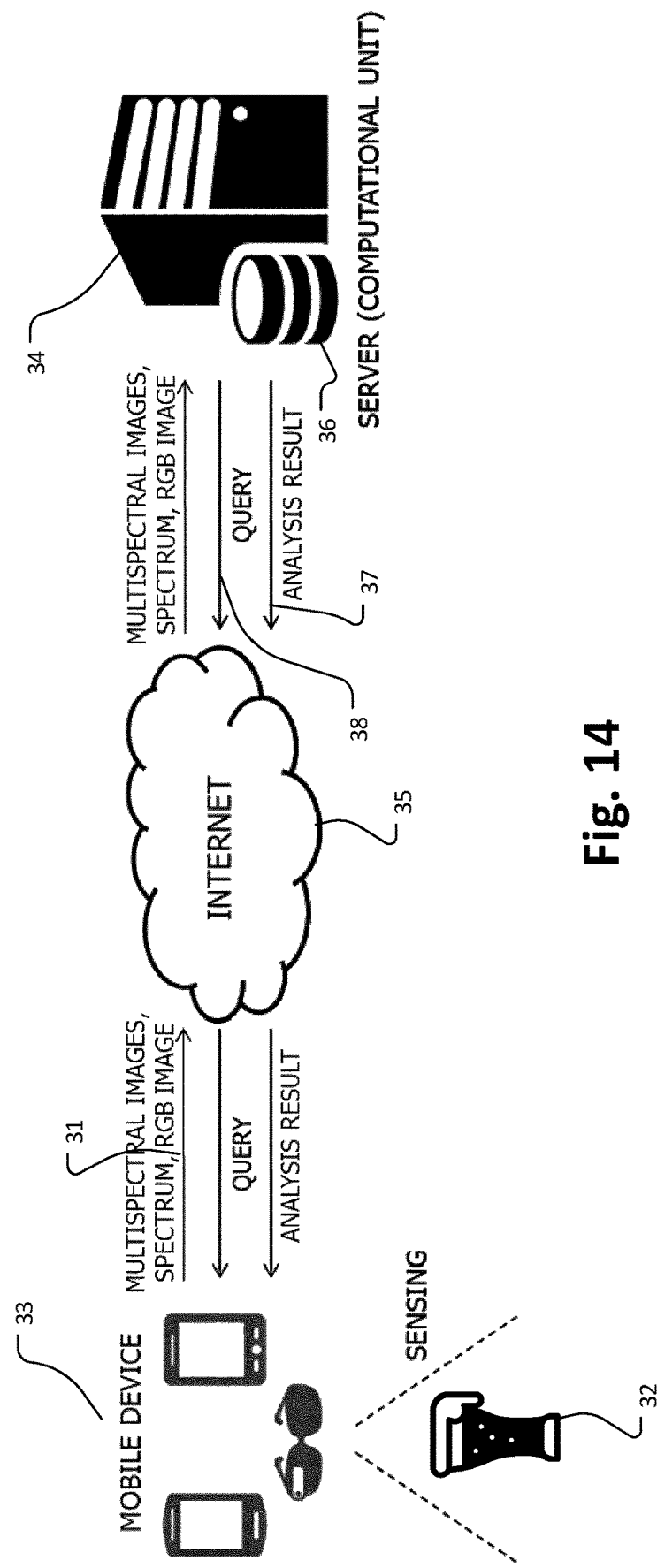
FIG. 14 schematically describes an embodiment of a system for feedback generation via Internet using user feedback.

FIG. 14 schematically describes an embodiment of a system for feedback generation via Internet using user feedback. The system generates an analysis result 37 with interactive feedback from a user. Multispectral images, a spectrum, and/or an RGB image 31 of a beverage 32 are captured by a multispectral imaging device, by a spectral imager or, respectively, by a RGB camera mounted on a smart device 33. The measured data 31 is transferred to computational unit 34 via the Internet 35. At the computational unit 34, it is determined that the information is not enough to determine an analysis result. Accordingly, the system sends a query 38 with some guidance for asking a user to change the capturing setting (i.e. to capture the beverage differently). The query 38 can for example be an advice for changing the attitude of camera. After enough information to provide feedback has been acquired, the system generates an analysis result 37 and sends it to a user.

Calibration Process

There are situations of beverage/liquid analysis in which a calibration phase is beneficial or even required, e.g. if a colored drinking glass is used or a glass is very thick. In case of a colored drinking glass the color (which corresponds to its filter characteristics) of the glass will affect the spectral evaluation in an unwanted manner and thus it is helpful to determine the color (respectively spectral transmission characteristics) of the glass such that the spectral analysis can be compensated for it.

Figure 15A:
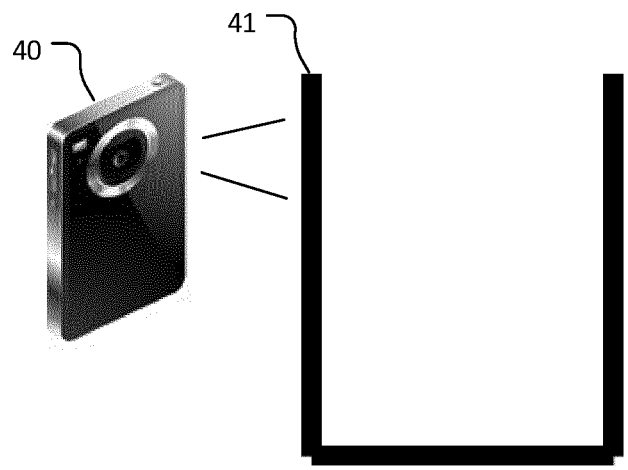
FIGS. 15a,b disclose embodiments, where a calibration is performed which allows to enhance the results of beverage/liquid analysis.

FIG. 15*a* discloses a first embodiment, where a calibration is performed which allows to enhance the results of beverage/liquid analysis. In this first embodiment, in a calibration phase, a spectral camera 40 (for example mounted on a mobile device) determines the color of a glass 41 before serving when the glass is empty.

Figure 15B:
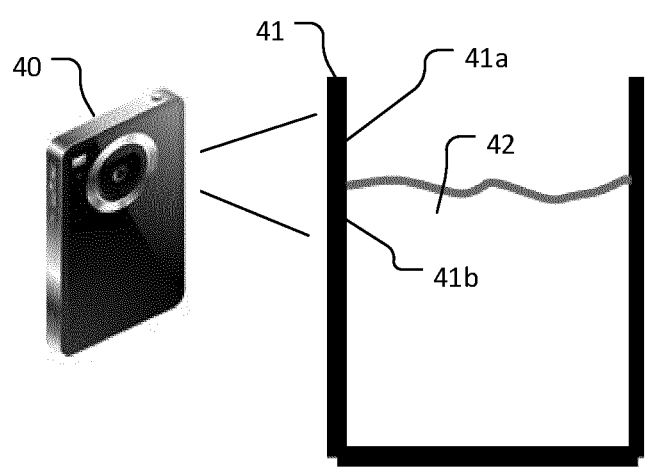

FIG. 15*b* discloses a second embodiment, where a calibration is performed which allows to enhance the results of beverage/liquid analysis. In this second embodiment, in a calibration phase, a spectral camera 40 determines the color of a glass 41 after serving. The glass 41 is not completely filled up with liquid 42. As indicated in FIG. 13*b*, the spectral camera 40 captures an area 41*a* of the glass 40 where no liquid 42 is present, and an area 41*b* of the glass 40 where liquid 42 is present. The calibration is performed based on the part of the spectral image in which the area 41*a* is captured. According to yet another embodiment, the calibration and evaluation is done in one shot by evaluating the two different areas 41*a* and 41*b* of the spectral image, i.e. upper part 41*a* for calibration and lower part 42*b* for the beverage analysis.

All units and entities described in this specification and claimed in the appended claims can, if not stated otherwise, be implemented as integrated circuit logic, for example on a chip, and functionality provided by such units and entities can, if not stated otherwise, be implemented by software.

The methods as described herein are also implemented in some embodiments as a computer program causing a computer and/or a processor to perform the method, when being carried out on the computer and/or processor. In some embodiments, also a non-transitory computer-readable recording medium is provided that stores therein a computer program product, which, when executed by a processor, such as the processor described above, causes the methods described herein to be performed.

It should be recognized that the embodiments describe methods with an exemplary order of method steps. The specific order of method steps is, however, given for illustrative purposes only and should not be construed as binding.

The method can also be implemented as a computer program causing a computer and/or a processor to perform the method, when being carried out on the computer and/or processor. In some embodiments, also a non-transitory computer-readable recording medium is provided that stores therein a computer program product, which, when executed by a processor, such as the processor described above, causes the method described to be performed.

In so far as the embodiments of the disclosure described above are implemented, at least in part, using a software-controlled data processing system, it will be appreciated that a computer program providing such software control and a transmission, storage or other medium by which such a computer program is provided are envisaged as aspects of the present disclosure.

Note that the present technology can also be configured as described below:

(1) A system including
circuitry configured to
determine a reflectance feature of a liquid based on reflectance image data generated based on multispectral image data of the liquid;
determine a structural feature of the liquid based on image data of the liquid; and to
provide quality information of the liquid based on the reflectance feature and the structural feature.

(2) The system of (1) wherein the multispectral image data includes first multispectral image data of a liquid without calibrated light and second multispectral image data of the liquid with calibrated light.

(3) The system of (1) or (2) wherein the circuitry is configured to obtain the first multispectral image data of the liquid without calibrated light.

(4) The system of (1) or (2) wherein the circuitry is configured to obtain the second multispectral image data of the liquid with calibrated light.

(5) The system of (2) wherein the circuitry is configured to generate spectral difference image data based on the first multispectral image data and the second multispectral image data.

(6) The system of (5) wherein the circuitry is configured to generate the reflectance image data from the spectral difference image data.

(7) The system of (5) wherein the circuitry is configured to determine the image data from the spectral difference image data.

(8) The system of (1) wherein the determination of the structural feature of the liquid based on the image data includes a bubble and/or foam analysis.

(9) The system of (1) wherein the structural feature of the liquid includes structural information of a bubble and/or foam of the liquid.

(10) The system of (1) wherein the circuitry is configured to obtain the image data of the liquid and wherein determining a structural feature of the liquid from the image data includes performing a bubble and/or foam analysis.

(11) The system of (1) wherein the circuitry is configured to process the multispectral image data of the liquid to obtain information on the contents of the liquid.

(12) The system of (1) wherein the circuitry is configured to generate, based on the obtained information, a query with guidance to change image capture settings.

(13) The system of (12) wherein the circuitry is configured to generate the query with guidance according to insufficient information on the contents of the liquid.

(14) The system of (11) wherein the circuitry is configured to generate feedback concerning the liquid based on the obtained information on the contents of the liquid.

(15) The system of (1) further including a sensor arrangement configured to collect the multispectral image data of the liquid.

(16) The system of (1) wherein the sensor arrangement includes an image obtaining unit capable of obtaining a multispectral image, and/or a spectral image.

(17) The system of (1) wherein the sensor arrangement is configured to provide visible images, infrared images, and/or spectral data.

(18) The system of (1), wherein the circuitry is configured to guide a user to change an attitude of a camera to point to other components of the liquid.

(19) The system of (1), wherein the circuitry is configured to guide the user to change the shooting angle of a camera.

(20) The system of (1), wherein the circuitry is configured to guide the user to move a camera and to see a particular components of the liquid close up.

(21) The system of (1), wherein the circuitry is configured to generate feedback concerning the liquid based on the obtained information on the contents of the liquid.

(22) The system of (21), wherein the feedback includes ingredients information, nutrition information, allergen information, and/or information on the quality of the liquid.

(23) The system of (1), further including a sensor arrangement configured to collect the multispectral image data of the liquid.

(24) The system of (23), wherein the sensor arrangement includes an image obtaining unit capable of obtaining a multispectral image, and/or a spectral image.

(25) The system of (24), wherein the sensor arrangement further includes an RGB image sensor.

(26) The system of (24), wherein the sensor arrangement is configured to provide visible images, infrared images, and/or spectral data.

(27) The system of (1), wherein the circuitry is configured to provide visible images, infrared images, and/or spectral data.

(28) The system of (1), wherein the circuitry is configured to communicate with a remote apparatus based on the quality information of the liquid.

(29) The system of (1), wherein the circuitry is configured to contact a maintenance service of a liquid processing machine based on an analysis of the reflectance features.

(30) A method including
determining a reflectance feature of a liquid based on reflectance image data generated based on multispectral image data of the liquid;
determining a structural feature of the liquid based on image data of the liquid; and
providing quality information of the liquid based on the reflectance feature and the structural feature.

(31) A computer program including instructions, the instructions when executed on a processor causing the processor to
determine a reflectance feature of a liquid based on reflectance image data generated based on multispectral image data of the liquid;
determine a structural feature of the liquid based on image data of the liquid; and to
provide quality information of the liquid based on the reflectance feature and the structural feature.

The invention claimed is:

1. A system comprising
circuitry configured to
determine a reflectance feature of a liquid based on reflectance image data generated based on multispectral image data of the liquid, wherein the multispectral image data comprises first multispectral image data of the liquid without calibrated light and second multispectral image data of the liquid with calibrated light;
determine a structural feature of the liquid based on image data of the liquid; and to
provide quality information of the liquid based on the reflectance feature and the structural feature.

2. The system of claim 1 wherein the circuitry is configured to obtain the first multispectral image data of the liquid without calibrated light.

3. The system of claim 1 wherein the circuitry is configured to obtain the second multispectral image data of the liquid with calibrated light.

4. The system of claim 1 wherein the circuitry is configured to generate spectral difference image data based on the first multispectral image data and the second multispectral image data.

5. The system of claim 4 wherein the circuitry is configured to generate the reflectance image data from the spectral difference image data.

6. The system of claim 4 wherein the circuitry is configured to determine the image data from the spectral difference image data.

7. The system of claim 1 wherein determining the structural feature of the liquid based on the image data comprises a bubble and/or foam analysis.

8. The system of claim 1 wherein the structural feature of the liquid comprises structural information of a bubble and/or foam of the liquid.

9. The system of claim 1 wherein the circuitry is configured to obtain the image data. of the liquid and wherein determining a structural feature of the liquid from the image data comprises performing a bubble and/or foam analysis.

10. The system of claim 1 wherein the circuitry is configured to process the multispectral image data of the liquid to obtain information on contents of the liquid.

11. The system of claim 10 wherein the circuitry is configured to generate, based on the obtained information, a query with guidance to change image capture settings.

12. The system of claim 11 wherein the circuitry is configured to generate the query with guidance according to insufficient information on the contents of the liquid.

13. The system of claim 10, wherein the circuitry is configured to generate feedback concerning the liquid based on the obtained information on the contents of the liquid.

14. The system of claim 1, further comprising a sensor arrangement configured. to collect the multispectral image data of the liquid.

15. The systemof claim 14, wherein the sensor arrangement comprises an image obtaining unit capable of obtaining a multispectral image, and/or a spectral image.

16. The system of claim 15, wherein the sensor arrangement further comprises an RGB image sensor.

17. The system of claim 15, wherein the sensor arrangement is configured to provide visible images, infrared images, and/or spectral data.

18. The system of claim 1, wherein the circuitry is configured to control an actuator for modifying a liquid processing based on the quality information of the liquid.

19. The system of claim 1, wherein the circuitry is configured to communicate with a remote apparatus based on the quality information of the liquid.

20. A method comprising
determining a reflectance feature of a liquid based on reflectance image data generated based on multi spectral image data of the liquid, wherein the multispectral image data comprises first multispectral image data of the liquid without calibrated light and second multi spectral image data of the liquid with calibrated light;
determining a structural feature of the liquid based on image data of the liquid; and
providing quality information of the liquid based on the reflectance feature and the structural feature.

21. A non-transitory computer-readable medium including a computer program comprising instructions, the instructions when executed on a processor causing the processor to:
- determine a reflectance feature of a liquid based on reflectance image data generated based on multi spectral image data of the liquid, wherein the multispectral image data comprises first multispectral image data of the liquid without calibrated light and second multispectral image data of the liquid with calibrated light;
- determine a structural feature of the liquid based on image data of the liquid; and to
- provide quality information of the liquid based on the reflectance feature and the structural feature.

* * * * *